US012796985B2

(12) United States Patent
Yu et al.

(10) Patent No.: US 12,796,985 B2
(45) Date of Patent: Nov. 17, 2026

(54) MULTIMODAL POSITION TRANSFORMATION DUAL-HELMET MEG APPARATUS

(71) Applicant: Korea Research Institute of Standards and Science, Daejeon (KR)

(72) Inventors: Kwon-Kyu Yu, Daejeon (KR); Yong-Ho Lee, Daejeon (KR); Hyukchan Kwon, Daejeon (KR); Jin-Mok Kim, Daejeon (KR); Sang-Kil Lee, Daejeon (KR); Bokyung Kim, Daejeon (KR); Min-Young Kim, Daejeon (KR); Kiwong Kim, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 42 days.

(21) Appl. No.: 19/043,533

(22) Filed: Feb. 3, 2025

(65) Prior Publication Data

US 2025/0176886 A1 Jun. 5, 2025

Related U.S. Application Data

(60) Division of application No. 17/853,827, filed on Jun. 29, 2022, now Pat. No. 12,245,858, which is a (Continued)

(30) Foreign Application Priority Data

Jun. 11, 2020 (KR) ........................ 10-2020-0070698

(51) Int. Cl.

*A61B 5/245* (2021.01)
*A61B 5/00* (2006.01)
*G01R 33/32* (2006.01)

(52) U.S. Cl.

CPC ............ *A61B 5/245* (2021.01); *A61B 5/4064* (2013.01); *A61B 5/6803* (2013.01);
(Continued)

(58) Field of Classification Search

CPC ..... A61B 5/245; A61B 5/4064; A61B 5/6803; G01R 33/34; G01R 33/326
See application file for complete search history.

(56) References Cited

U.S. PATENT DOCUMENTS 4,700,135 A * 10/1987 Hoenig ............. G01R 33/0358 324/248
5,381,122 A * 1/1995 Laskaris ........... G01R 33/3806 324/318
(Continued)

FOREIGN PATENT DOCUMENTS

CN 110891482 A 3/2020
KR 101007498 B1 1/2011
(Continued)

OTHER PUBLICATIONS

International Search Report dated Jun. 30, 2021; International Patent Application No. PCT/KR2021/002451; 3 pgs.; Korean Intellectual Property Office, Daejeon, Republic of Korea.

*Primary Examiner* — John D Li
(74) *Attorney, Agent, or Firm* — Central California IP Group, P.C.; Andrew D. Fortney

(57) ABSTRACT

A dual-helmet magnetoencephalography measuring apparatus according to an example embodiment includes: an internal container storing a liquid refrigerant; an external container disposed to surround the internal container and including a first external helmet and a second external helmet disposed to be spaced apart from each other; a first sensor-mounted helmet disposed between the external container and the internal container to surround the first external helmet; a second sensor-mounted helmet disposed between the external container and the internal container to surround the second external helmet; a plurality of first SQUID sensor modules disposed on the first sensor-mounted helmet; and a plurality of second SQUID sensor modules disposed on the
(Continued)

second sensor-mounted helmet. The internal container and the external container are tilted in a vertical direction.

18 Claims, 23 Drawing Sheets

Related U.S. Application Data continuation of application No. PCT/KR2021/002451, filed on Feb. 26, 2021.

(52) U.S. Cl.
CPC . *A61B 2562/0223* (2013.01); *A61B 2562/066* (2013.01); *G01R 33/326* (2013.01)

(56) References Cited

U.S. PATENT DOCUMENTS

| | | | | |
|---|---|---|---|---|
| 5,388,580 | A | 2/1995 | Sullivan et al. | |
| 5,713,354 | A | 2/1998 | Warden | |
| 9,823,312 | B2 | 11/2017 | Yu et al. | |
| 10,585,151 | B2 | 3/2020 | Yu et al. | |
| 11,766,204 | B2 | 9/2023 | Burton et al. | |
| 2005/0272996 | A1 | 12/2005 | Matsui et al. | |
| 2012/0252678 | A1* | 10/2012 | Kim | G01R 33/326 62/51.1 |
| 2013/0090241 | A1* | 4/2013 | Harrison | H01F 6/04 324/322 |
| 2015/0268311 | A1 | 9/2015 | Yu et al. | |
| 2016/0003507 | A1* | 1/2016 | Kim | F28D 7/10 62/524 |
| 2016/0174862 | A1 | 6/2016 | Yu et al. | |
| 2016/0223622 | A1* | 8/2016 | Yu | G01R 33/0354 |
| 2017/0067969 | A1 | 3/2017 | Butters et al. | |
| 2017/0168121 | A1 | 6/2017 | Yu et al. | |
| 2018/0242865 | A1 | 8/2018 | Yamagata | |
| 2020/0196887 | A1 | 6/2020 | Burton et al. | |
| 2022/0330869 | A1 | 10/2022 | Yu et al. | |

FOREIGN PATENT DOCUMENTS

| | | | |
|---|---|---|---|
| KR | 20140054638 | A | 5/2014 |
| KR | 20150047680 | A | 5/2015 |
| KR | 20160031349 | A | 3/2016 |

* cited by examiner

MULTIMODAL POSITION TRANSFORMATION DUAL-HELMET MEG APPARATUS

CROSS-REFERENCE TO RELATED APPLICATIONS

This application is a divisional of U.S. patent application Ser. No. 17/853,827, filed Jun. 29, 2022, pending, which is a continuation of and which claims priority to PCT/KR2021/002451, filed on Feb. 26, 2021, which claims priority to Korea Patent Application No. KR 10-2020-0070698, filed on Jun. 11, 2020, the entireties of which are incorporated herein by reference.

TECHNICAL FIELD

The present disclosure relates to a magnetoencephalography apparatus and, more particularly, to a magnetoencephalography apparatus provide with dual helmets.

BACKGROUND

A magnetoencephalography apparatus is an apparatus for measuring magnetic signals generated by microcurrent of cerebral neural circuits, and is used to study brain functions and to diagnose functional brain diseases.

In general, a magnetoencephalography signal has an amplitude of 10 fT to 1 pT and has a frequency of 0.1 to 1 kHz. Accordingly, there is a requirement for a magnetic sensor having improved sensitivity and a technology to cancel environmental magnetic noise. At present, a magnetic sensor which is most advantageous in practical terms is a superconducting quantum interference device (SQUID) based on a low-temperature superconductor niobium (Nb).

Since Nb used for a low-temperature superconducting SQUID has a critical temperature of 9 K, cooling using liquid helium or a low-temperature freezer is required. Current magnetoencephalography apparatuses need to supplement liquid helium. Optimization of a structure, a thickness, and an installing method of a material is required to reduce thermal magnetic noise, caused by a superinsultion and thermal shield installed in a Dewar vacuum portion, while reducing an evaporation rate of a Dewar. In addition, since helium gas tends to easily pass through a small gap, high density of glass fiber reinforced plastics, used as a material of the Dewar, is required.

Since the intensity of a magnetic signal from a magnetic field signal source decreases in inverse proportion to the square of a distance, a distance between the signal source and a pick-up coil needs to be significantly reduced to increase a signal-to-noise ratio (SNR). Research into such a method has been conducted to develop and use a coil-in-vacuum (CIV) SQUID in which a pick-up coil is disposed in a vacuum vessel.

In a CIV SQUID apparatus, a pick-up coil and a SQUID sensor are disposed to be maintained in a vacuum state. Accordingly, only a low-temperature refrigerant is present in an internal helium storage container for storing a liquid refrigerant. Accordingly, there is only a path to fill the refrigerant. Accordingly, a diameter of a neck portion of the internal helium storage container may be significantly reduced. As a result, an evaporation rate of the liquid refrigerant may be reduced.

SUMMARY

An aspect of the present disclosure is to provide a cooling apparatus having a dual-wall structure, capable of blocking radiant heat.

Another aspect of the present disclosure is to provide a cooling apparatus, capable of recycling a refrigerant.

Another aspect of the present disclosure is to provide a magnetoencephalography apparatus provided with two helmets.

Another aspect of the present disclosure is to provide a magnetoencephalography apparatus, provided with two helmets having different sizes, capable of selecting a lying state and a sitting state.

Another aspect of the present disclosure is to provide a magnetoencephalography apparatus, provided with two helmets having different sizes, capable of selecting a measuring angle.

Another aspect of the present disclosure is to provide a main thermal anchor preventing damage caused by a difference in coefficient of thermal expansion.

Another aspect of the present disclosure is to provide a stable support structure of a dual-helmet magnetoencephalography apparatus having a Y-shaped structure.

A dual-helmet magnetoencephalography measuring apparatus according to an example embodiment includes: an internal container storing a liquid refrigerant; an external container disposed to surround the internal container and including a first external helmet and a second external helmet disposed to be spaced apart from each other; a first sensor-mounted helmet disposed between the external container and the internal container to surround the first external helmet; a second sensor-mounted helmet disposed between the external container and the internal container to surround the second external helmet; a plurality of first SQUID sensor modules disposed on the first sensor-mounted helmet; and a plurality of second SQUID sensor modules disposed on the second sensor-mounted helmet. The internal container and the external container are tilted in a vertical direction.

In an example embodiment, the external container may branch off in the form of Y. One of the first external helmet and the second external helmet may be parallel to measure a lying person, and the other of the first external helmet and the second external helmet may be tilted to measure a sitting person.

In an example embodiment, the dual-helmet magnetoencephalography measuring apparatus may further include: a rotational motion unit coupled to the external container to rotate the external container about a central axis of the external container.

In an example embodiment, the dual-helmet magnetoencephalography measuring apparatus may further include: a tilt adjustment unit coupled to the rotational motion unit to adjust a tilt to a vertical direction of the external container; and a support portion supporting the tilt adjustment unit.

In an example embodiment, the dual-helmet magnetoencephalography measuring apparatus may further include: a first reference SQUID sensor module mounted on the first sensor-mounted helmet; and a second reference SQUID sensor module disposed on the second sensor-mounted helmet. Each of the first reference SQUID sensor module and the second reference SQUID sensor module may include a triaxial magnetic field sensor.

In an example embodiment, the internal container may include: a neck portion into which a baffle insert is inserted; and a body portion having an increased diameter as compared with the neck portion. The neck portion may have a double-wall structure including an internal cylinder and an external cylinder surrounding the internal cylinder.

In an example embodiment, the dual-helmet magnetoencephalography measuring apparatus may further include: a refrigerant exhaust tube disposed at the baffle insert and exhausting an evaporated refrigerant; a refrigerant injection tube disposed at the baffle insert and injecting a refrigerant; and a condenser connected to the refrigerant exhaust tube and the refrigerant injection tube and condensing an evaporated refrigerant exhausted through the refrigerant injection tube. The refrigerant exhaust tube and the refrigerant injection tube may have a coaxial structure. Each of the refrigerant exhaust tube and the refrigerant injection tube may be a dual tube including an internal tube and an external tube.

A magnetoencephalography measuring apparatus according to an example embodiment includes: an internal container storing a liquid refrigerant; an external container disposed to surround the internal container and including a first external helmet and a second external helmet disposed to be spaced apart from each other; a first sensor-mounted helmet disposed between the external container and the internal container to surround the first external helmet; a second sensor-mounted helmet disposed between the external container and the internal container to surround the second external helmet; a plurality of first SQUID sensor modules disposed on the first sensor-mounted helmet; and a plurality of second SQUID sensor modules disposed on the second sensor-mounted helmet. Each of the plurality of first SQUID sensor modules is in thermal contact with a main thermal anchor, disposed on a lower surface of the internal container, through a litz wire. Each of the plurality of second SQUID sensor modules is in thermal contact with the main thermal anchor, disposed on the lower surface of the internal container, through a litz wire. A space between the external container and the internal container is in a vacuum state.

In an example embodiment, the external container may include a first branch and a second branch branching off from a cylindrical external container body portion in the form of Y. The first external helmet and the second external helmet may be coupled to the first branch and the second branch, respectively.

In an example embodiment, the external container body portion may be disposed to be tilted in a vertical direction. The first external helmet and the second external helmet may be disposed to be spaced apart from each other at an interval of 110 degrees, based on central axes of the first external helmet and the second external helmet.

In an example embodiment, the external container body portion may rotate about a central axis of the external container body portion. The first external helmet may be applied to a subject in a sitting state or a lying state, depending on a rotation state of the external container.

In an example embodiment, the magnetoencephalography measuring apparatus may further include: a rotational motion unit coupled to an external side surface of the external container body portion. The rotational motion unit may be fixed to a ceiling of a magnetically shielded room.

In an example embodiment, the first external helmet may be provided with a long groove in a coupling portion of the first external helmet. The first external helmet may rotate along the long groove to be coupled to one end of the first branch while being aligned with the first branch, and the second external helmet may be provided with a long groove in a coupling portion of the second external helmet. The second external helmet may rotate along the groove to be coupled to one end of the second branch while being aligned with the second branch.

In an example embodiment, the magnetoencephalography measuring apparatus may further include: a washer-shaped first fixing ring disposed to be vertically spaced apart from the first sensor-mounted helmet; a plurality of first support pillars connecting the first fixing ring and a brim of the first sensor-mounted helmet to each other; a washer-shaped second fixing ring disposed to be vertically spaced apart from the second sensor-mounted helmet; a plurality of second support pillars connecting the second fixing ring and a brim of the second sensor-mounted helmet to each other; a helmet alignment support portion disposed to be spaced apart from a lower surface of the internal container; and a plurality of fixing ring support portion fixing the first fixing ring and the second fixing ring to the helmet alignment support portion.

In an example embodiment, the helmet alignment support portion may be provided with a plurality of ring-shaped curved long grooves. A coupling member may be inserted into each of the curved long grooved and is coupled to the lower surface of the internal container.

In an example embodiment, the magnetoencephalography measuring apparatus may further include: a first auxiliary thermal anchor disposed on a lower surface of a brim of the first sensor-mounted helmet; a first internal 4K heat shielding portion being in thermal contact with the first auxiliary thermal anchor and disposed on an internal side surface of the first sensor-mounted helmet; a first external 4K heat shielding portion being in thermal contact with the first auxiliary thermal anchor and disposed on an external side surface of the first sensor-mounted helmet; a second auxiliary thermal anchor disposed on a lower surface of a brim of the second sensor-mounted helmet; a second internal 4K heat shielding portion being in thermal contact with the second auxiliary thermal anchor and disposed on an internal side surfaced of the second sensor-mounted helmet; and a second external 4K heat shielding portion being in thermal contact with the second auxiliary thermal anchor and disposed on an external side surface of the second sensor-mounted helmet. The first auxiliary thermal anchor, the first internal 4K heat shielding portion, and the first external 4K heat shielding portion may be in thermal contact with the main thermal anchor through a litz wire. The second auxiliary thermal anchor, the second internal 4K heat shielding portion, and the second external 4K heat shielding portion may be in thermal contact with the main thermal anchor through a litz wire.

In an example embodiment, the first SQUID sensor module may be cooled by a plurality of litz wires. Some of the plurality of litz wires are provided to a neighboring first SQUID sensor module, and the remainder of the plurality of litz wires may be in thermal contact with the main thermal anchor.

In an example embodiment, the first SQUID sensor module may be cooled by six litz wires. Two litz wires may be in thermal contact with the main thermal anchor, and four litz wires may be provided to a neighboring first SQUID sensor module.

In an example embodiment, the internal container may include: a neck portion into which a baffle insert is inserted; an upper body portion having an increased diameter as compared with the neck portion; and a lower body portion having a decreased diameter as compared with the upper body portion. The neck portion may have a double-wall structure.

In an example embodiment, the magnetoencephalography measuring apparatus may further include: washer-shaped first to third thermal anchors sequentially disposed outside the neck portion to be vertically spaced apart from each other. The first thermal anchor is connected to a 120K heat shielding layer, the second thermal anchor is connected to an 80K heat shielding layer, and the third thermal anchor is connected to a 40K heat shielding layer. The 40K heat shielding layer may be disposed to cover the first sensor-mounted helmet and the second sensor-mounted helmet.

In an example embodiment, each of the first to third thermal anchors may have a plurality of slits extending in a radial direction.

In an example embodiment, the first SQUID sensor module may be inserted into a through-hole, formed in the first sensor-mounted helmet, to be fixed. Each of the first SQUID sensor modules may have a plurality of holes. The litz wire may be inserted into the holes to cool a SQUID sensor.

In an example embodiment, the magnetoencephalography measuring apparatus may further include: a rotational motion unit coupled to an external side of the external container body portion; a tilt adjustment unit coupled to the rotational motion unit to adjust a tilt to a vertical direction of the external container; and a support portion supporting the tilt adjustment unit.

In an example embodiment, the main thermal anchor may include: a first heat transfer unit formed of oxygen-free copper and including a first disc, a first upper projection protruding from a central axis of the first disc to an upper surface of the first disc, and a first lower projection protruding from the central axis of the first disc to a lower surface of the first disc; a second heat transfer unit formed of oxygen-free copper and including a second disc, a second upper projection protruding from a central axis of the second disc to an upper surface of the second disc, a second lower projection protruding from the central axis of the second disc to a lower surface of the second disc; a third heat transfer unit formed of oxygen-free copper and including a third disc, a third upper projection protruding from a central axis of the third disc to an upper surface of the third disc, and a third lower projection protruding from the central axis of the third disc to a lower surface of the third disc; a fourth heat transfer unit formed of oxygen-free copper and including a fourth disc, a fourth upper projection protruding from a central axis of the fourth disc to an upper surface of the fourth disc, and a fourth lower projection protruding from the central axis of the fourth disc to a lower surface of the fourth disc; a first thermal expansion control unit formed of an insulating material and inserted between the first disc of the first heat transfer unit and the second disc of the second heat transfer unit; and a second thermal expansion control unit formed of an insulating material and disposed between the third disc of the third heat transfer unit and the fourth disc of the fourth heat transfer unit. The second upper projection of the second heat transfer unit may be provided with a groove for coupling to the lower projection of the first heat transfer unit, the second lower projection of the second heat transfer unit may be provided with a groove for coupling to the third upper projection of the third heat transfer unit, and the third lower projection of the third heat transfer unit may be provided with a groove for coupling to the fourth upper projection of the fourth heat transfer unit.

In an example embodiment, the first thermal expansion control unit may include: a first insulating body portion having the same diameter as a first diameter of the first disc; a second insulating body portion embedded in a lower surface of the internal body and having a second diameter greater than the first diameter; and a third insulating body portion having a third diameter smaller than the second diameter. The third insulating body portion may be disposed to cover an external circumferential surface of the second disc.

A magnetic field measuring apparatus according to an example embodiment includes: an external container; and an internal container storing a liquid refrigerant and inserted into the external container. The internal container includes: a neck portion into which a baffle insert is inserted; and a body portion having an increased diameter as compared with the neck portion. The neck portion has a double-wall structure including an internal cylinder and an external cylinder surrounding the internal cylinder.

In an example embodiment, the internal cylinder may further include a plurality of ring projections protruding outwardly of a cylinder. Thermal anchors may be coupled to the ring projections, respectively. The ring projections may be disposed to be spaced apart from each other. The external cylinder may be divided with the ring projection interposed therebetween.

In an example embodiment, the neck portion may further include a heat shielding layer disposed between the internal cylinder and the external cylinder.

In an example embodiment, an external circumferential surface of the ring projection and an internal circumferential surface of the thermal anchor may be screw-coupled to each other.

In an example embodiment, the thermal anchor may include a cylindrical thermal anchor coupling portion and a disc-shaped thermal anchor body portion disposed on an external circumferential surface of the thermal anchor coupling portion. An internal circumferential surface of the thermal anchor coupling portion may be screw-coupled to an external circumferential surface of the ring projection.

In an example embodiment, each of the thermal anchors may have a plurality of slits, extending from an external circumferential surface in an internal radial direction, and a groove extending from one end of the slit in an azimuthal direction.

In an example embodiment, the thermal anchor may include first to third thermal anchors. The first thermal anchor may be connected to a 120K heat shielding layer, the second thermal anchor may be connected to an 80K heat shielding layer, and the third thermal anchor may be connected to a 40K heat shielding layer.

In an example embodiment, the magnetic field measuring apparatus may further include: a refrigerant exhaust tube disposed at the baffle insert and exhausting an evaporated refrigerant; a refrigerant injection tube disposed at the baffle insert and injecting a refrigerant; and a condenser connected to the refrigerant exhaust tube and the refrigerant injection tube and condensing an evaporated refrigerant exhausted through the refrigerant injection tube. Each of the refrigerant exhaust tube and the refrigerant injection tube may be a dual tube including an internal tube and an external tube.

A magnetic field measuring apparatus according to an example embodiment includes: an external container; an internal container storing a liquid refrigerant and inserted into the external container; a baffle insert inserted into the internal container; a refrigerant exhaust tube disposed at the baffle insert and exhausting an evaporated refrigerant; a refrigerant injection tube disposed at the baffle insert and injecting a refrigerant; and a condenser connected to the refrigerant exhaust tube and the refrigerant injection tube and condensing an evaporated refrigerant exhausted through the refrigerant injection tube. The refrigerant exhaust tube and the refrigerant injection tube have a coaxial structure. Each of the refrigerant exhaust tube and the refrigerant injection tube is a dual tube including an internal tube and an external tube.

In an example embodiment, the internal container may include: a neck portion into which a baffle insert is inserted; and a body portion having an increased diameter as compared with the neck portion. The neck portion may have a double-wall structure including an internal cylinder and an external cylinder surrounding the internal cylinder.

A magnetic field measuring apparatus according to an example embodiment includes: an external container; an internal container storing a liquid refrigerant and inserted into the external container; a main thermal anchor disposed on a lower surface of the internal container; and a plurality of first SQUID sensor modules disposed outside the internal container. Each of the plurality of is in thermal contact with a main thermal anchor, disposed on the lower surface of the internal container, through a litz wire.

In an example embodiment, the main thermal anchor may include: a first heat transfer unit formed of oxygen-free copper and including a first disc, a first upper projection protruding from a central axis of the first disc to an upper surface of the first disc, and a first lower projection protruding from the central axis of the first disc to a lower surface of the first disc; a second heat transfer unit formed of oxygen-free copper and including a second disc, a second upper projection protruding from a central axis of the second disc to an upper surface of the second disc, a second lower projection protruding from the central axis of the second disc to a lower surface of the second disc; a third heat transfer unit formed of oxygen-free copper and including a third disc, a third upper projection protruding from a central axis of the third disc to an upper surface of the third disc, and a third lower projection protruding from the central axis of the third disc to a lower surface of the third disc; a fourth heat transfer unit formed of oxygen-free copper and including a fourth disc, a fourth upper projection protruding from a central axis of the fourth disc to an upper surface of the fourth disc, and a fourth lower projection protruding from the central axis of the fourth disc to a lower surface of the fourth disc; a first thermal expansion control unit formed of an insulating material and inserted between the first disc of the first heat transfer unit and the second disc of the second heat transfer unit; and a second thermal expansion control unit formed of an insulating material and disposed between the third disc of the third heat transfer unit and the fourth disc of the fourth heat transfer unit. The second upper projection of the second heat transfer unit may be provided with a groove for coupling to the lower projection of the first heat transfer unit, the second lower projection of the second heat transfer unit may be provided with a groove for coupling to the third upper projection of the third heat transfer unit, and the third lower projection of the third heat transfer unit may be provided with a groove for coupling to the fourth upper projection of the fourth heat transfer unit.

In an example embodiment, the first thermal expansion control unit may include: a first insulating body portion having the same diameter as a first diameter of the first disc; a second insulating body portion embedded in a lower surface of the internal body and having a second diameter greater than the first diameter; and a third insulating body portion having a third diameter smaller than the second diameter. The third insulating body portion may be disposed to cover an external circumferential surface of the second disc.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
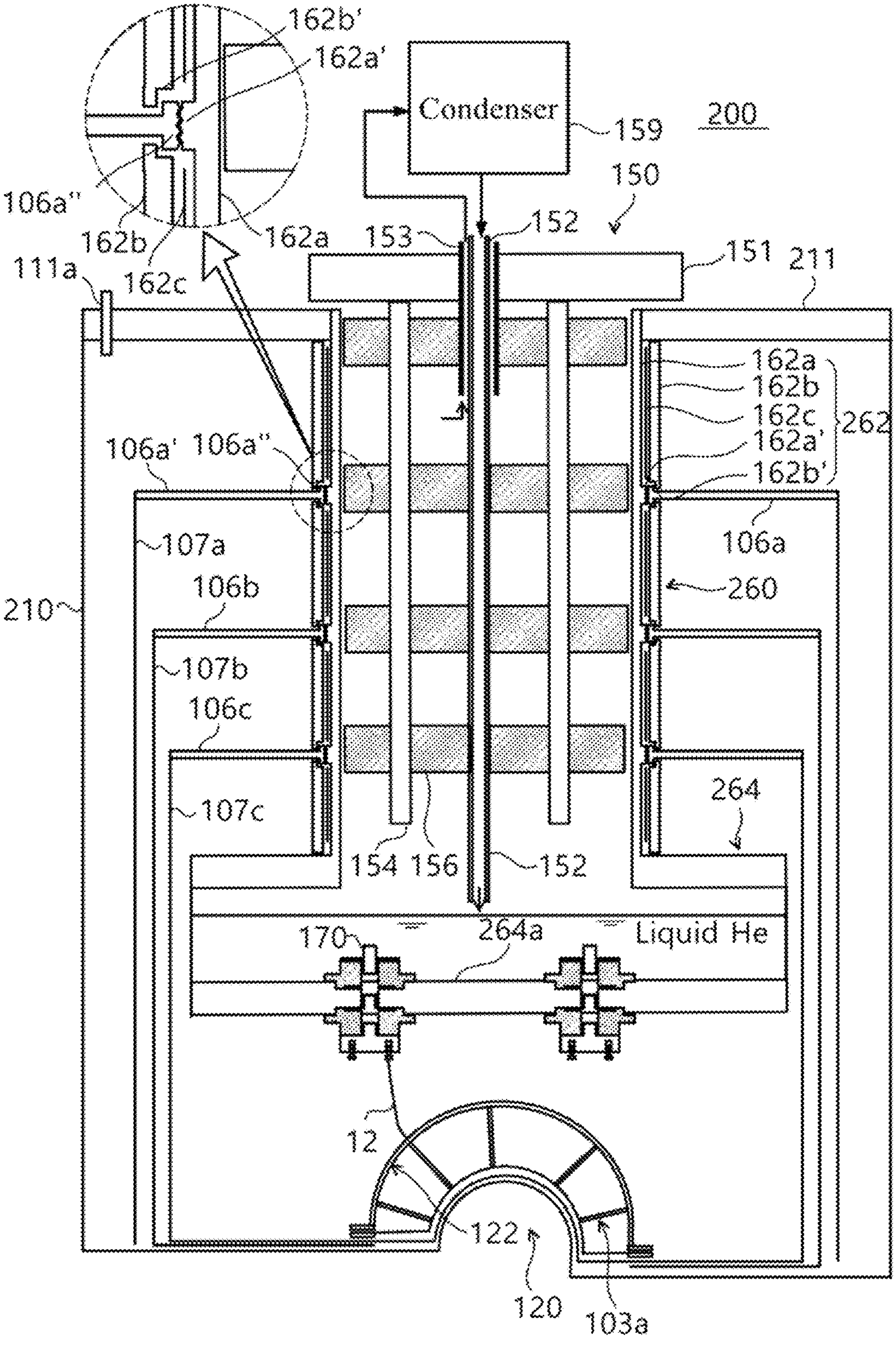
FIG. 1 is a conceptual diagram illustrating a magnetic field measuring apparatus according to an example embodiment of the present disclosure.

According to an example embodiment, a technology for directly recondensing a helium gas using a refrigerator and resending the recondensed helium gas to a Dewar is applied.

Since magnetic noise and vibration noise caused by the refrigerator and refrigerant delivery tube are significantly large, a special Dewar structure and a special SQUID arrangement method are required to prevent a SQUID from reacting with vibrations.

With the recent increase in the price of helium gas, a technology for directly recondensing a helium gas using a refrigerator and resending the recondensed helium gas to a magnetoencephalography Dewar is required. Evaporated helium is supplied to a refrigerator through a refrigerant exhaust tube, and a liquefied refrigerant is supplied to a Dewar through a refrigerant injection tube. When the refrigerant exhaust tube and the refrigerant injection tube include a single pipe, ice is condensed on a baffle insert lid. Such ice inhibits perfect sealing to causes lots of external heat influx.

A CIV SQUID according to an example embodiment addresses an issue regarding ice condensation on a baffle insert lid using a coaxial dual-tube structure. A refrigerant exhaust tube and a refrigerant injection tube have a coaxial structure, and each of the refrigerant exhaust tube and the refrigerant injection tube has a dual-tube structure. The dual-tube structure a cold evaporated gas to a cooler to increase cooling efficiency. In addition, a coaxial dual tube may provide a rotational motion using a sealing member such as an O-ring.

In the CIV SQUID, a Dewar includes an internal container and an external container surrounding the internal container. However, the internal container absorbs radiant heat externally to increase consumption of a refrigerant.

In the CIV SQUID, the Dewar uses a double-wall structure in a neck portion of the internal container into which a baffle insert is inserted. Such a double-wall structure may make a significant contribution to prevent vacuum break caused by thermal shrinkage of components, constituting an interior of the Dewar, during rapid cooling. In the double-wall structure, a vacuum layer is automatically formed when the interior of the Dewar is cooled and, in order to reduce influx of radiant heat, a heat shielding layer is provided between double walls to significantly reduce influx of radiant heat from a neck of the Dewar. Screw coupling is used to bring an effective thermal contact with an internal wall of an internal container of the double-wall structure and to reduce damage caused by thermal expansion. The double-wall structure may reduce an evaporation rate of a refrigerant and may stably support an internal structure with a high load, inhibiting nose caused by evaporation of the refrigerant and external vibration.

A magnetoencephalography (MEG) signal depends on a distance between a SQUID sensor and a brain. Therefore, an MEG helmet for adults is inappropriate for measurement of children's MEG. Accordingly, there is demand for a dual-helmet structure allowing a single MEG apparatus to measure both adults' MEG and children's MEG.

A helmet for children is provided with 144 channels, and a helmet for adults is provided with 192 channels. Therefore, as a structure optimized for a head size, a dual-helmet structure is expected to have improved quality. In addition, such a dual-helmet structure is advantageous in measuring a development process from children to adults.

A magnetoencephalography apparatus according to an example embodiment of the present disclosure has a structure in which a single Dewar is provided with two helmets. A helmet for children and a helmet for adults, having different sizes, are mounted to be spaced apart from each other at an angle of about 110 degrees in a Dewar body tilted about 35 degrees. A central axis of the helmet for children is mounted to be spaced apart from a central axis of a Dewar at an angle of 125 degrees, and a central axis of the helmet for adults is mounted to be spaced apart from the central axis of the Dewar at an angle of 125 degrees. That is, the central axis of the helmet for children is mounted to be spaced apart from the central axis of the helmet for adults at an angle of 110 degrees.

In the magnetoencephalography apparatus, the helmet for children and the helmet for adults may measure a subject in a sitting state and a lying state, respectively. To this end, the Dewar body may rotate about the central axis of the Dewar. Accordingly, the helmet for children may measure the subject in a sitting state, or the helmet for adults may measure the subject in a sitting state.

In the magnetoencephalography apparatus, the helmet for children and the helmet for adults may each measure magnetoencephalography (MEG) in a sitting state or MEG in a lying state. That is, the measurement of MEG in the sitting state may be performed while applying a visual stimulus to a subject. In addition, the magnetoencephalography apparatus may adjust a tilt of a sitting position.

A magnetoencephalography apparatus according to an example embodiment of the present disclosure may include a helmet for adults and a helmet for children. A triaxial reference SQUID sensor may be provided in each of the helmets. When the helmet for adults operates, background noise may be removed using the triaxial SQUID sensor provided in the helmet for children.

In the magnetoencephalography apparatus, each of the helmet for children and the helmet for adults may measure MEG in a lying state and MEG in a sitting state, depending on a rotation state of the Dewar. A rotational motion unit may provide a rotational motion of the Dewar using a non-metallic bearing.

A magnetoencephalography apparatus according to an example embodiment of the present disclosure may include a main thermal anchor disposed on a lower surface of an internal container. The main thermal anchor may include a plurality of heat transfer portions, screw-coupled to each other, and a thermal expansion control portion formed of an insulating material and controlling sealing fracture caused by thermal expansion between the heat transfer portion and the internal container. When the plurality of heat transfer portions are coupled to each other, a pair of thermal expansion control portions, disposed to be embedded in an external surface and an internal surface of the internal container, are pressed to inhibit damage to components caused by sealing and thermal expansion.

Hereinafter, embodiments of the present disclosure will be described below more fully with reference to accompanying drawings. The present disclosure may, however, be embodied in different forms and should not be constructed as limited to the embodiments set forth herein. Rather, these embodiments are provided so that this disclosure will be thorough and complete, and will fully convey the scope of the present invention to those skilled in the art.

FIG. 1 is a conceptual diagram illustrating a magnetic field measuring apparatus according to an example embodiment of the present disclosure.

Figure 2:
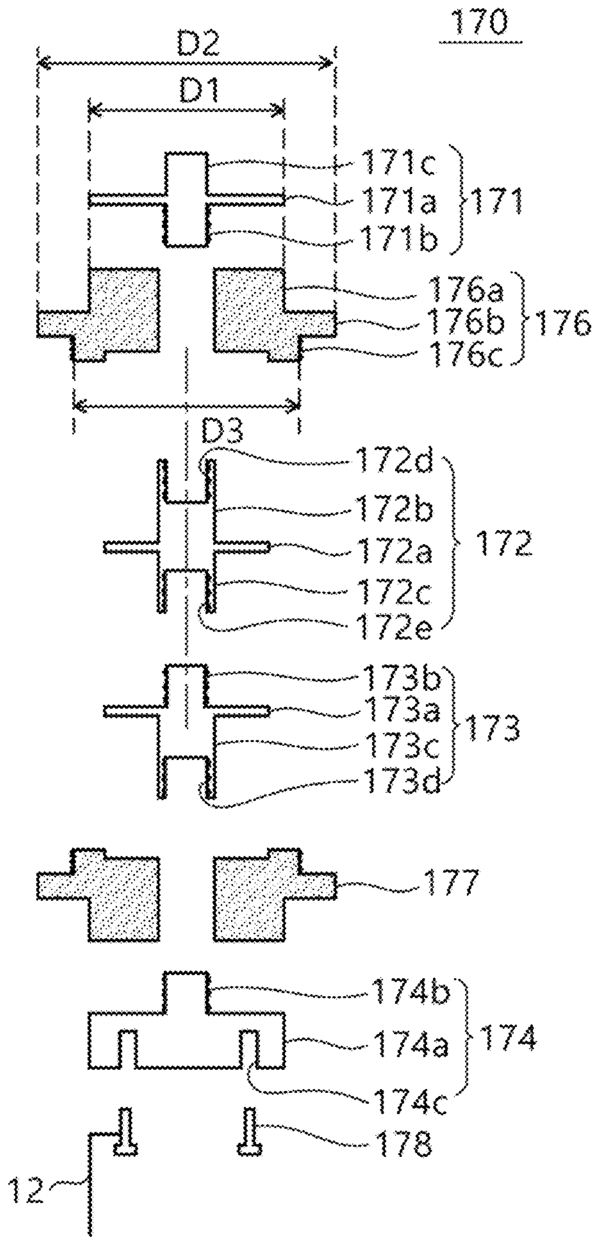
FIG. 2 is a conceptual diagram illustrating a main thermal anchor of a magnetic field measuring apparatus according to an example embodiment of the present disclosure.

FIG. 2 is a conceptual diagram illustrating a main thermal anchor of a magnetic field measuring apparatus according to an example embodiment of the present disclosure.

Referring to FIGS. 1 and 2, a magnetic field measuring apparatus 200 includes an external container 210 and an internal container 260 storing a liquid refrigerant and inserted into the external container 210. The internal container 260 includes a neck portion 262, into which a baffle insert 150 is inserted, and a body portion 264 having an increased diameter as compared with the neck portion 262. The neck portion 262 is a double-wall structure including an internal cylinder and an external cylinder surrounding the internal cylinder.

The external container 210 may have a cylindrical shape and may include at least one external helmet 120. The external helmet 120 may be disposed on a lower surface of the external container 210. A sensor-mounted helmet 122 corresponding to the external helmet 210 may be disposed between the external container 210 and the internal container 260. The external container 210 employs glass fiber reinforced epoxy, and may be a G-10 epoxy. The G-10 epoxy may be used as a material of a low-temperature refrigerant storage container for biomagnetic measurement.

The external container 210 may include an external container lid 211. The external container lid 211 may have a through-hole in a center thereof. The internal container 260 may be coupled to the through-hole of the external container lid 211.

The internal container 260 includes a neck portion 262 and a body portion 264 having an increased diameter as compared with the neck portion 262. The internal container 260 may store a liquid refrigerant. The internal container 260 may be formed of G-10 epoxy.

The neck portion 262 has a double-wall structure. That is, the neck portion 262 may include an internal cylinder 162*a* and an external cylinder 162*b* surrounding the internal cylinder 162*a*. The heat shielding layer 162*c* may be disposed between the internal cylinder 162*a* and the external cylinder 162*b*. The heat shielding layer 162*c* may be a metal mesh woven with metal wires insulated from each other.

The internal cylinder 162*a* may further include a plurality of ring projections 162*a*' protruding outwardly of a cylinder. The ring projection 162*a*' has a cylindrical ring shape, and may be formed to be integrated with the internal cylinder 162*a*. A screw for screw-coupling may be formed on an external circumferential surface of the ring projection 162*a*'.

The ring projections 162*a*' may be disposed to be spaced apart from each other. The external cylinders 162*b* may be separated from each other with the ring projection 162*a*' interposed therebetween. That is, the external cylinder 162*b* may include a plurality of cylindrical components separated from each other. A distance between the external cylinder 162*b* and the internal cylinder 162*a* may be within several millimeters (mm). Each of the external cylinders 162*b* may include a thermal anchor coupling portion 106*a*" and a raised portion 162*b*' to surround the ring projection 162*a*'. After the external cylinder 162*b* is coupled to surround the ring projection 162*a*', a coupling portion may be fixed and sealed with an adhesive such as epoxy.

Thermal anchors 106*a*, 106*b*, and 106*c* may be coupled to each of the ring projections 162*a*'. The external circumferential surface of the ring projection 162*a*' and an internal circumferential surface of the column anchor 106*a* may be screwed-coupled to each other. Each of the thermal anchors 106*a*, 106*b*, and 106*c* may have a circular washer shape. The thermal anchors 106*a*, 106*b*, 106*c* may include copper or aluminum.

The thermal anchor 106*a* may include a cylindrical thermal anchor coupling portion 106*a*" and a disc-shaped thermal anchor body portion 106*a*' disposed on an external circumferential surface of the coupling portion 106*a*". The internal circumferential surface of the thermal anchor coupling portion 106*a*" may be screw-coupled to the external circumferential surface of the ring projection 162*a*'. The screw-coupling of the ring projection 162*a*' and the thermal anchor 106*a* may improve mechanical stability while providing efficient thermal contact brought by thermal expansion.

The double-wall structure may block the influx of radiant heat into the neck portion 262 from an external entity. When the inside of the double-wall structure is cooled by a refrigerant, a space between the internal cylinder 162*a* and the external cylinder 162*b* may be maintained in a vacuum state. Accordingly, heat influx heat caused by heat transfer may be blocked, and the heat shielding layer 162*c* may additionally block radiant heat influx. As a result, the neck portion 262 of the double-wall structure may provide high mechanical stability and high thermal shielding efficiency, as compared with a neck portion of a single-wall structure.

The thermal anchors 106*a*, 106*b*, and 106*c* may include first to third thermal anchors 106*a*, 106*b*, and 106*c* disposed in order. The first thermal anchor 106*a* may be disposed on an uppermost side of a neck portion, and may be connected to a 120K heat shielding layer 107*a*. The second thermal anchor 106*b* may be disposed below the first thermal anchor 106*a*, and may be connected to an 80K heat shielding layer 107*b*. The third thermal anchor 106*c* may be disposed below the second thermal anchor 106*b*, and may be connected to a 40K heat shielding layer 107*c*.

The first thermal anchor 106*a* is farthest spaced apart from the refrigerant to be maintained at a highest temperature, and the third thermal anchor 106*c* may be closest to the refrigerant to be maintained at a lowest temperature. The first to third thermal anchors 106*a*, 106*b*, and 106*c* may be in thermal contact with an evaporated refrigerant to be cooled.

The 40K heat shielding layer 107*c* may be coupled to an external circumferential surface of the third thermal anchor 106*c*, may be disposed to surround the internal container 260 and to block the radiant heat influx. The 40K heat shielding layer 107*c* may include a metal mesh, woven with metal wires insulated from each other, and a heat insulation film.

The 80K heat shielding layer 107*b* may be coupled to an external circumferential surface of the second thermal anchor 106*b*, and may be disposed to surround the 40K heat shielding layer 107*a* and to block the radiant heat influx. The 80K heat shielding layer 107*b* may include a metal mesh, woven with metal wires insulated from each other, and a heat insulation film.

The 120K heat shielding layer 107*a* may be coupled to an external circumferential surface of the first thermal anchor 106*a*, and may be disposed to surround the 80K heat shielding layer 107*b* and to block the radiant heat influx. The 120K heat shielding layer 107*a* may include a metal mesh, woven with metal wires insulated from each other, and a heat insulation film.

The space between the internal container 260 and the external container 210 may be maintained in a vacuum state. The external container lid 211 may include an exhaust port 111*a* connected to a vacuum pump. The exhaust port 111*a* may be formed of a G-10 epoxy tube.

The baffle insert 150 may be disposed to be inserted into the neck portion 262 of the internal container 260. The baffle insert 150 may include an insert upper plate 151, a baffle 156 disposed below the insert upper plate, and a plurality of guide rods 154 supporting the baffle 156 and fixed to the insert upper plate 151.

The insert upper plate 151 may have a disc shape and may be formed of G-10 epoxy. The insert upper plate 151 may be fixed to the external container lid 211. The guide rod 154 may be formed of G-10 epoxy, and may have a rod shape or a pipe shape. The guide rod 154 may support the baffle 156.

The baffle 156 may include Styrofoam having improved warmth retention and a conductive plate. The conductive plate may include an aluminum-coated Mylar layer and a copper layer sequentially stacked to block the radiant heat.

A refrigerant exhaust tube 153 may be disposed on the insert upper plate 151 of the baffle insert 150, and may exhaust the evaporated refrigerant. The refrigerant injection tube 152 may be disposed on the insert upper plate 151 of the baffle insert 150, and may inject a refrigerant. Each of the refrigerant exhaust tube 153 and the refrigerant injection tube 152 may be a dual tube including an internal tube and an external tube. The refrigerant exhaust tube 153 may remove ice condensation on the insert upper plate 151 of the baffle inset 150.

The refrigerant injection tube 152 may have a coaxial structure inserted into the refrigerant exhaust tube 153. Each of the refrigerant exhaust tube 153 and the refrigerant injection tube 152 may be formed of G-10 epoxy. The coaxial structure of the refrigerant exhaust tube 153 and the refrigerant injection tube 152 may provide a rotational motion using a sealing member such as an O-ring.

The condenser 159 may be connected to the refrigerant exhaust tube 153 and the refrigerant injection tube 152, and may condense the evaporated refrigerant exhausted through the refrigerant injection tube 153, and may inject the condensed refrigerant into the internal container 260 through the refrigerant injection tube 152. The condenser 159 may be disposed outside the magnetically shielded room.

Coaxial dual tubes 152 and 153 may reduce thermal contact with the insert upper plate 151 to reduce ice formation of the insert upper plate 151. When the refrigerant exhaust tube and the refrigerant injection tube are a single tube, the insert upper plate 151 and the refrigerant exhaust tube may form ice to impede sealing of the external container lid 111 and the insert upper plate 151 and to increase influx of external heat. As the external container 310 rotates, the coaxial dual tubes 152 and 153 may provide sealing using a sealing means such as an O-ring.

The sensor-mounted helmet 122 may be disposed between a lower surface 264*a* of the internal container 260 and a lower surface of the external container 210. The SQUID sensor module 103*a* of the sensor-mounted helmet 122 may be cooled through thermal contact with the main thermal anchor 170.

According to a modified embodiment, the sensor-mounted helmet 122 may be modified in various forms as long as it may mount a SQUID sensor module. Therefore, a shape of the external container 210 may be changed into a corresponding shape. When the sensor-mounted helmet 122 has a plate shape, it may measure magnetoencephalography.

Referring to FIG. 2, the body portion 264 of the internal container 260 may have a lower surface 264*a*, and the main thermal anchor 170 may be disposed on a lower surface 264*a* of the body portion 264. The main thermal anchor 170 may include a conductive heat transfer material. The main thermal anchor 170 may be disposed to penetrate through the lower surface 264*a*.

The main thermal anchor 170 may include a first heat transfer unit 171, a second heat transfer unit 172, a third heat transfer unit 173, a fourth heat transfer unit 174, a first thermal expansion control unit 176, and a second thermal expansion control unit 177. The main thermal anchor 170 may include of a plurality of components to increases a thermal contact area while inhibiting damage to the internal container caused by thermal expansion, and thus, may efficiently cool a litz wire 12 and a SQUID sensor of the SQUID sensor module 103*a*.

The first thermal expansion control unit 176 may be coupled to a dual groove having two radii formed on an internal side of the lower surface of the internal container 260, and the second thermal expansion control unit 177 may be coupled to a dual groove having two radii formed on an external side of the lower surface of the internal container.

The first heat transfer unit 171 may be formed of oxygen-free copper, and may include a first disc 171*a* and a first lower projection 171*b* protruding from a central axis of the first disc 171*a* to a lower surface of the first disc 171*a*. The first heat transfer unit 171 may further include a first upper projection 171*c* protruding from the central axis of the first disc 171*a* to an upper surface of the first disc 171*a*.

The second heat transfer unit 172 may be formed of oxygen-free copper, and may include a second disc 172*a*, a second upper projection 172*b* protruding from a central axis of the second disc 172*a* to an upper surface of the second disc 172*a*, and a second lower projection 172*c* protruding from the central axis of the second disc 172*a* to a lower surface of the second disc 172*a*. The second upper projection 172*b* of the second heat transfer unit 172 may include a screw groove 172*d* for coupling to the first lower projection 171*b* of the first heat transfer unit 171. The second lower projection 172*c* of the second heat transfer unit 172 may have a screw groove 172*e* for coupling to the third upper projection 173*b* of the third heat transfer unit 173.

The third heat transfer unit 173 may be formed of oxygen-free copper, and may include a third disc 173*a*, a third upper projection 173*b* protruding from a central axis of the third disc 173*a* to an upper surface of the third disc 173*a*, and a third lower projection 173*c* protruding from the central axis of the third disc 173*a* to a lower surface of the third disc 173*a*. The third lower projection 173*c* of the third heat transfer unit 173 may have a screw groove 173*d* for coupling to the fourth upper projection 174*b* of the fourth heat transfer unit 174.

The fourth heat transfer unit 174 may be formed of oxygen-free copper, and may include a fourth disc and a fourth upper projection 174*b* protruding from a central axis of the fourth disc to an upper surface of the fourth disc. A lower surface of the fourth heat transfer unit 174 may be coupled to a fixing means 178. The fixing means 178 may fix and cool the litz wire 12 connected to the SQUID sensor module 103*a*.

The first thermal expansion control unit 176 may be formed of an insulating material, and may be inserted between the first disc 171*a* of the first heat transfer unit 171 and the second disc 172*b* of the second heat transfer unit 172. The first thermal expansion control unit 176 may be formed of the same material as the internal container 260.

The first thermal expansion control unit 176 may include a first insulating body portion 176*a* having the same diameter as a first diameter D1 of the first disc 171*a*, a second insulating body portion 176*b* embedded in buried in a lower surface of the internal body and having a second diameter D2 greater than the first diameter D1, and a third insulating body portion 176*c* having a third diameter D3 smaller than the second diameter D2. The third insulating body portion 176*c* may be disposed to surround an external circumferential surface of the second disc 172*a*. An external circumferential surface of the third insulating body portion 176*c* may have a screw groove.

The second thermal expansion control portion 177 may be formed of an insulating material, and may be inserted between the third disc 173*a* of the third heat transfer unit 173 and the fourth disc 174*a* of the fourth heat transfer unit 174.

The second thermal expansion control unit 177 may be formed of the same material as the internal container 260.

The second thermal expansion control unit 177 may have the same structure as the first thermal expansion control unit 176.

Each of the plurality of first SQUID sensor modules 103*a* may be in thermal contact with the main thermal anchor 170, disposed on the lower surface of the internal container 160, through the litz wire 12.

The SQUID sensor module 103*a* may be inserted into a through-hole, formed in the sensor mounting helmet 122, to be fixed. The SQUID sensor module 103*a* may have a plurality of holes. The litz wire 120 may be inserted into the holes to cool the SQUID sensor.

According to another example embodiment, the magnetic field measuring apparatus 200 may include an external container 210, a cylindrical internal container 260 storing a liquid refrigerant and inserted into the external container 210, a main thermal anchor 170 disposed on a lower surface of the internal container 260, and a plurality of SQUID sensor modules 103*a* disposed outside the internal container.

Each of the plurality of SQUID sensor modules 103*a* is in thermal contact with a main thermal anchor 170, disposed on the lower surface of the internal container 260, through a litz wire 12.

FIGS. 3A to 3D are conceptual diagrams illustrating a magnetoencephalography measuring apparatus according to an example embodiment of the present disclosure.

Referring to FIGS. 3A to 3D, a magnetoencephalography measuring apparatus 100 may include an internal container 160 storing a liquid refrigerant, an external container 110 disposed to surround the internal container 160 and including a first external helmet 120 and a second external helmet 130 disposed to be spaced apart from each other, a first sensor-mounted helmet 122 disposed between the external container 110 and the internal container 160 to surround the first external helmet 120, a second sensor-mounted helmet 132 disposed between the external container 110 and the internal container 160 to surround the second external helmet 130, a plurality of first SQUID sensor modules 103*a* disposed on the first sensor-mounted helmet 122, and a plurality of second SQUID sensor modules 103*b* disposed on the second sensor-mounted helmet 132. The magnetoencephalography measuring apparatus 100 may provide magnetoencephalography measurement in both cases of children and adults. The first external helmet 120 may be a helmet for children, and the second external helmet 130 may be a helmet for adults.

Figure 3A:
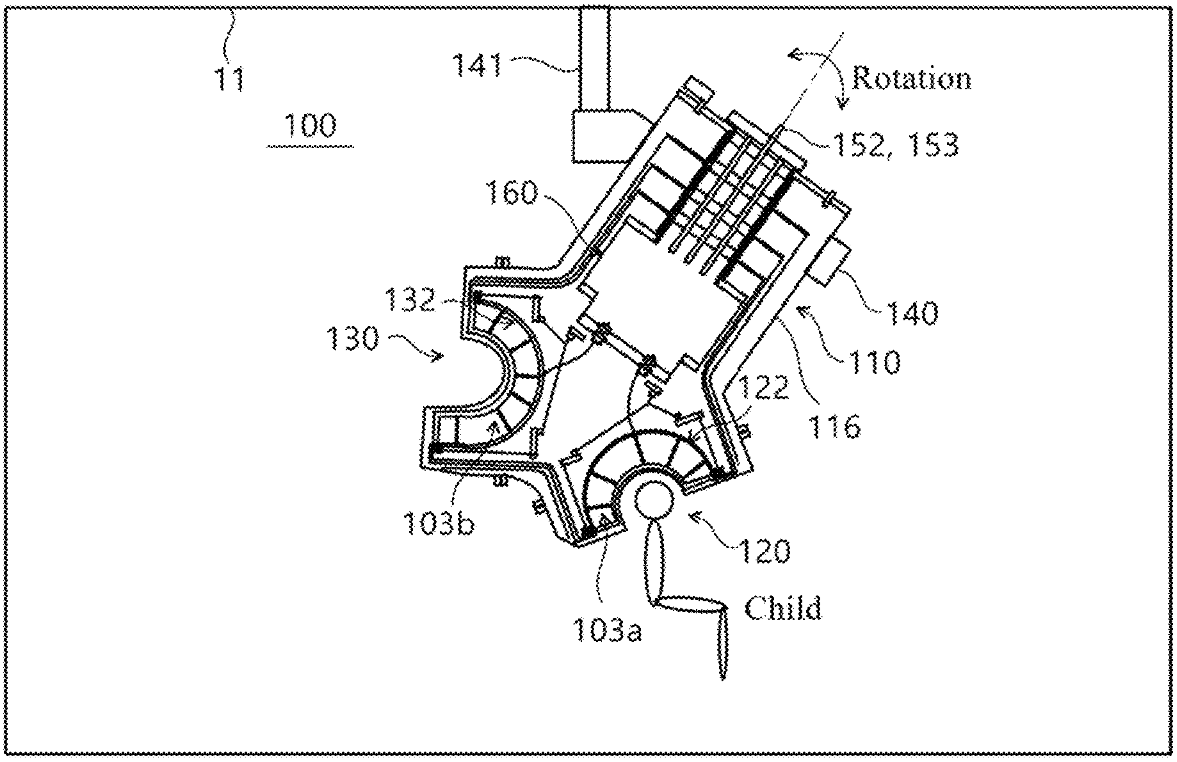
FIGS. 3A to 3D are conceptual diagrams illustrating a magnetoencephalography measuring apparatus according to an example embodiment of the present disclosure.

Referring to FIG. 3A, a child may be measured in a sitting position. Electroencephalography measurement in a sitting position may be performed to detect a response to an external stimulus. To this end, an external body portion 116 is tilted at a certain angle (35 degrees), and a helmet for children and a helmet for adults are spaced apart from each other at a certain angle (110 degrees). In addition, when a Dewar or the external container 110 rotates 180 degrees about a central axis thereof, a measurement position of the helmet for children and the helmet for adults are interchanged.

The external container body portion 116 may be disposed to be tilted at an angle of 30 degrees to 45 degrees in the vertical direction. The first external helmet 120 and the second external helmet 130 may be disposed to be spaced apart from each other at an interval of 110 degrees, based on central axes thereof. The internal container 160 and the external container 110 may be titled at an angle of 30 degrees to 45 degrees in the vertical direction. The internal container 160 and the external container 110 may be tilted at an angle of, in detail, 35 degrees in the vertical direction. Accordingly, the refrigerant stored in the internal container may also be tilted.

A rotational motion unit 140 may be coupled to the outside of the external container body portion 116. The rotational motion unit 140 may include a bearing formed of a non-conductive material. The rotational motion unit 140 may be fixed to a ceiling of a magnetically shielded room 11 through an external support portion 141.

Figure 3B:
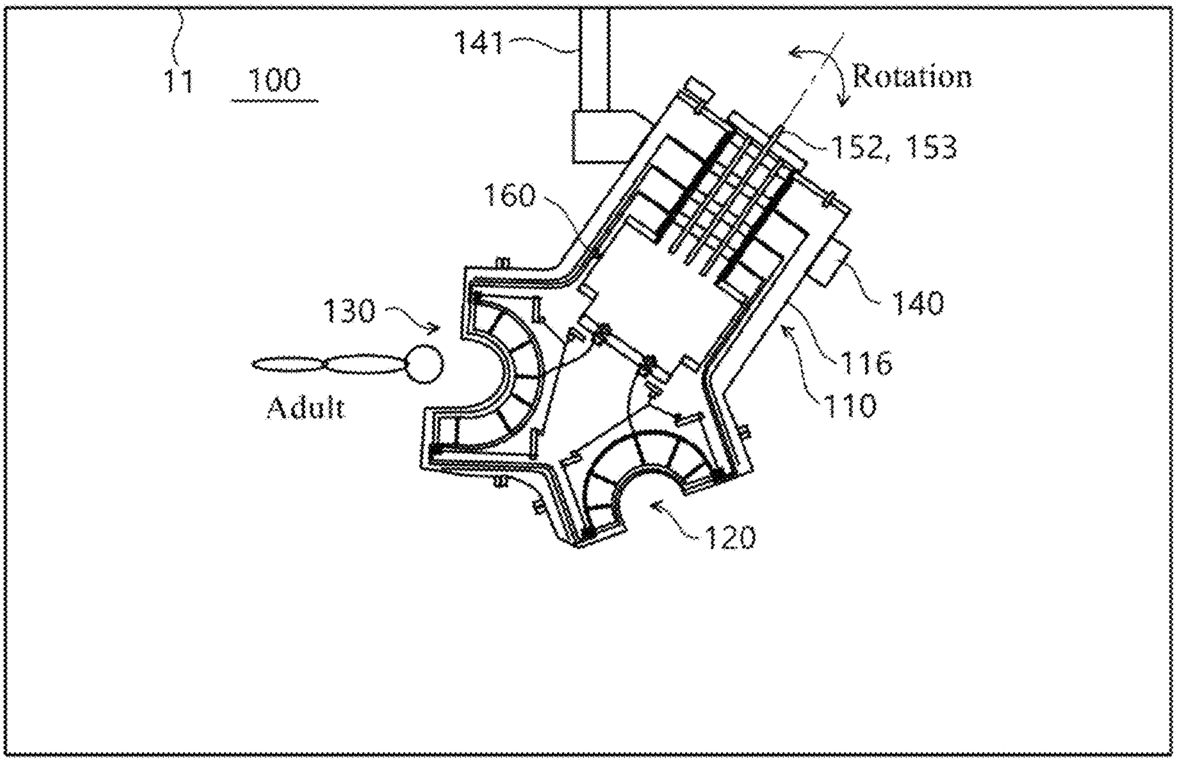

Referring to FIG. 3B, an adult may be measured in a lying position.

Figure 3C:
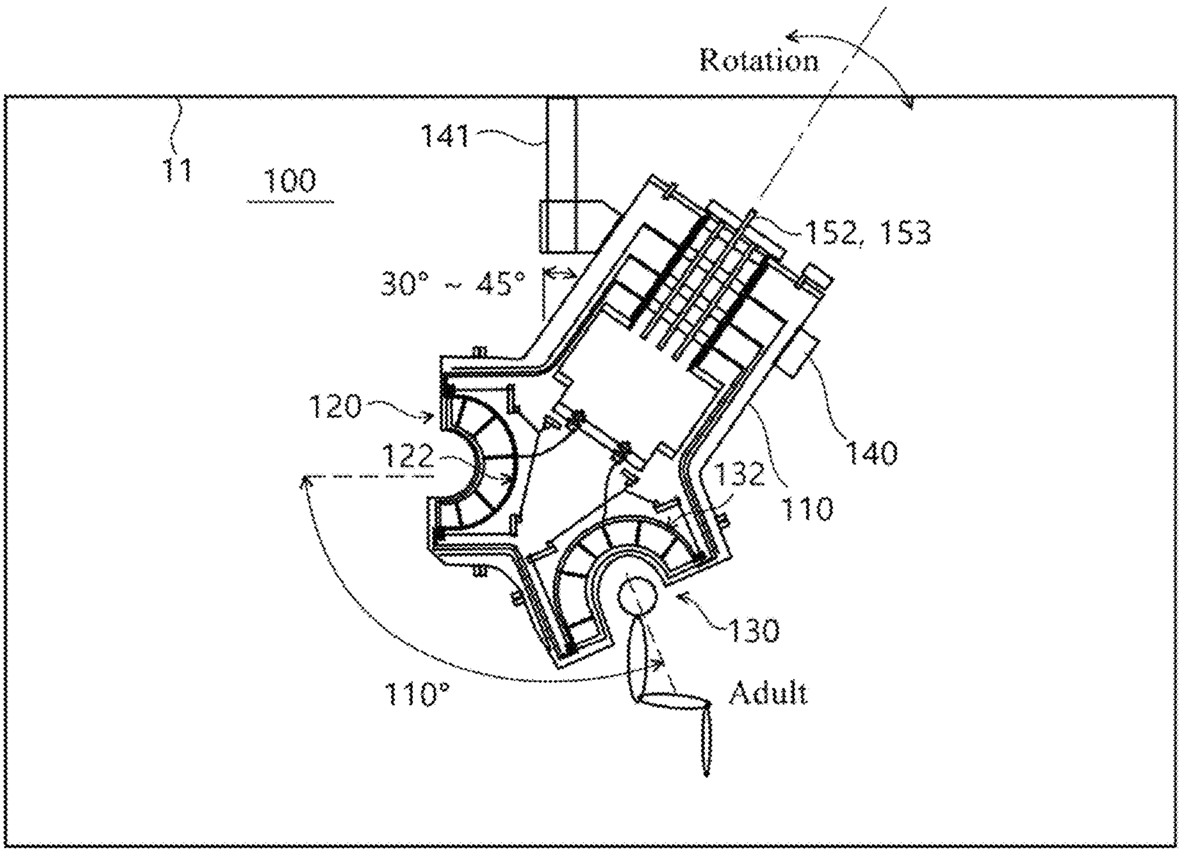

Referring to FIG. 3C, when the external container 110 of the magnetoencephalography measuring apparatus 100 rotates 180 degrees, an adult may be measured in a sitting position.

Figure 3D:
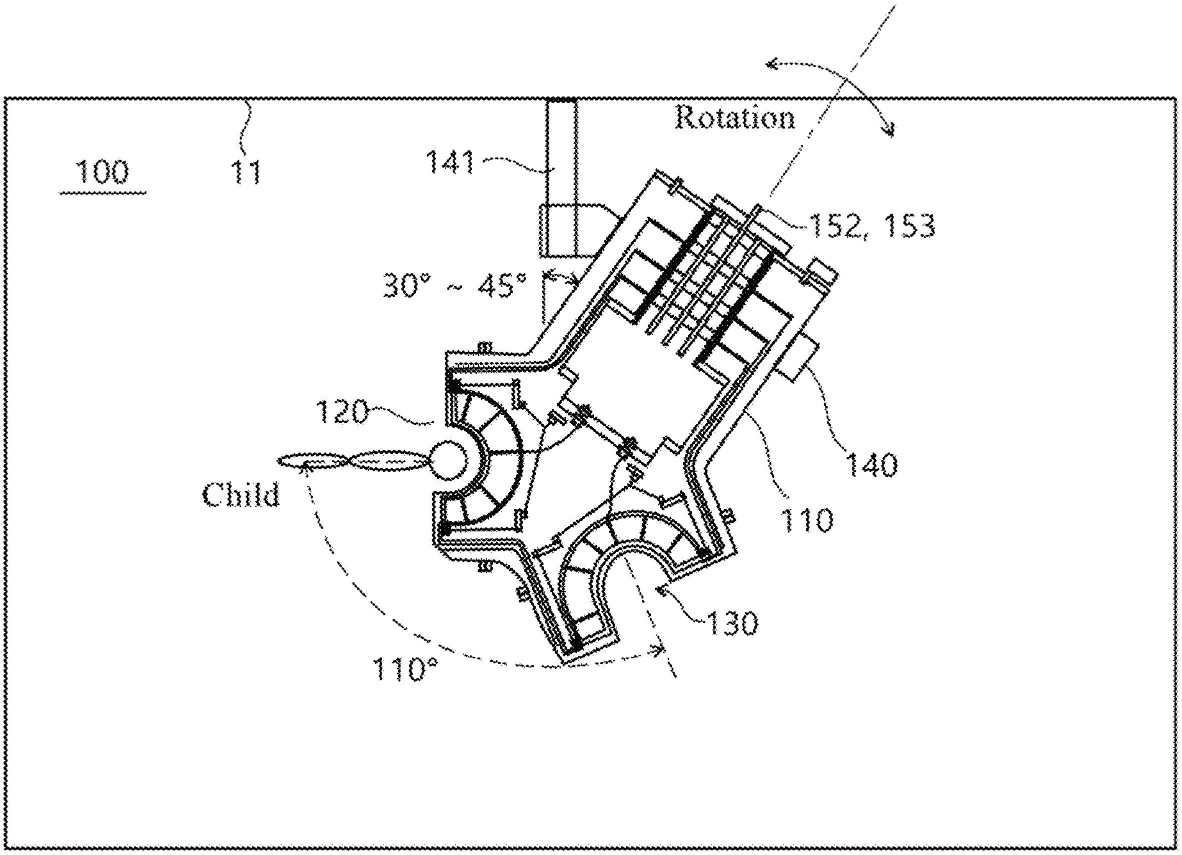

Referring to FIG. 3D, a child may be measured in a lying position.

Figure 4:
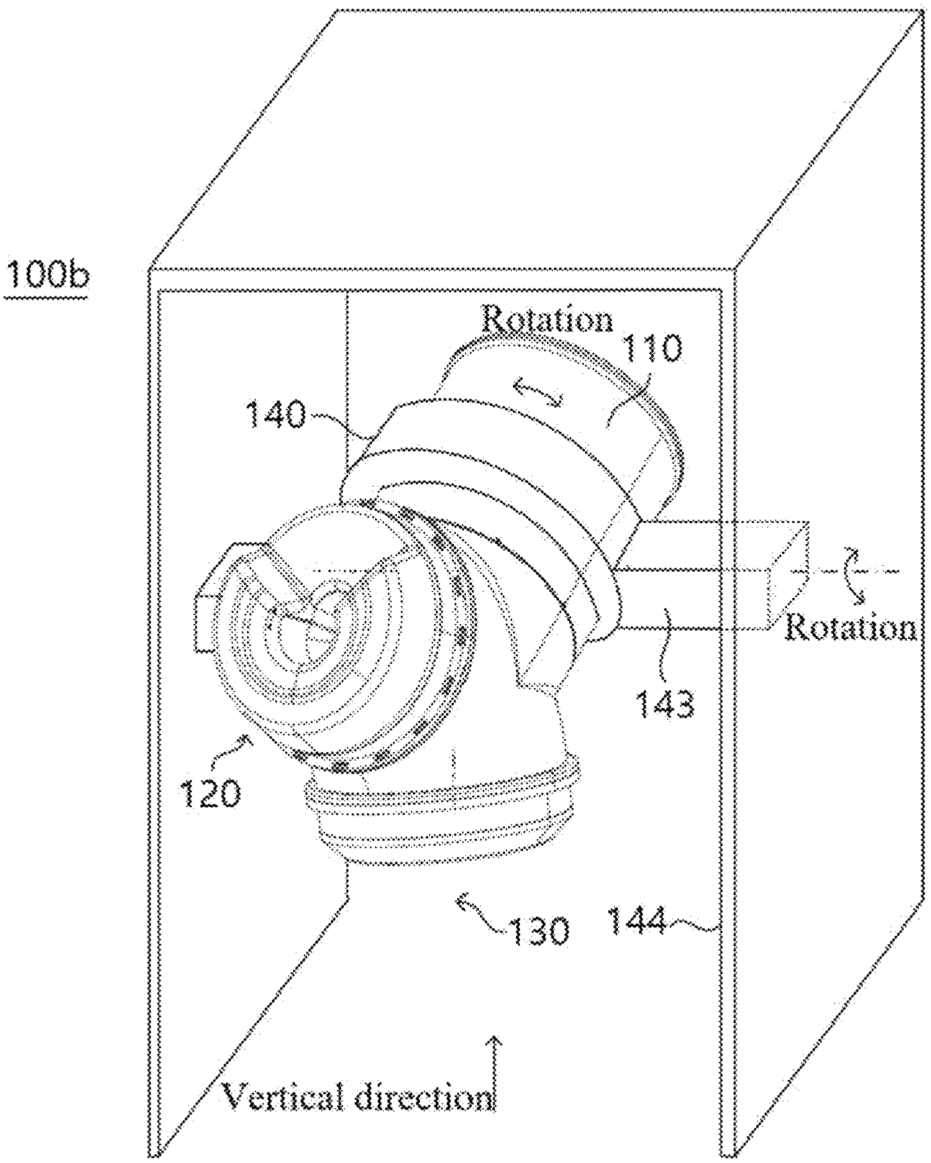
FIG. 4 is a perspective view illustrating a magnetoencephalography measuring apparatus according to another example embodiment of the present disclosure.

FIG. 4 is a perspective view illustrating a magnetoencephalography measuring apparatus according to another example embodiment of the present disclosure.

Referring to FIG. 4, a magnetoencephalography measuring apparatus 100*b* may include an internal container 160 storing a liquid refrigerant, an external container 110 disposed to surround the internal container 160 and including a first external helmet 120 and a second external helmet 130 disposed to be spaced apart from each other, a first sensor-mounted helmet 122 disposed between the external container 110 and the internal container 160 to surround the first external helmet 120, a second sensor-mounted helmet 132 disposed between the external container 110 and the internal container 160 to surround the second external helmet 130, a plurality of first SQUID sensor modules 103*a* disposed on the first sensor-mounted helmet 122, and a plurality of second SQUID sensor modules 103*b* disposed on the second sensor-mounted helmet 132. The magnetoencephalography measuring apparatus 100 may provide magnetoencephalography measurement in both cases of children and adults.

A rotational motion unit 140 may be coupled to the outside of the external container 110. The rotational motion unit 140 may include a bearing formed of a non-magnetic material. The rotational motion unit 140 may provide a rotational motion for selecting a measurement position, based on a central axis of the external container 110.

A tilt adjustment unit 143 may be coupled to the rotational motion unit 140 to adjust a tilt of the external container 110 in a vertical direction. The tilt adjustment unit 143 may provide a rotational motion about a horizontal axis. The tilt adjustment portion 143 may be coupled to a support portion 144 mounted in a magnetically shielded room 11. The support portion 144 may include a pair of partition walls. The tilt adjustment unit 143 may adjust a position of a helmet of a subject in a sitting state.

Figure 5:
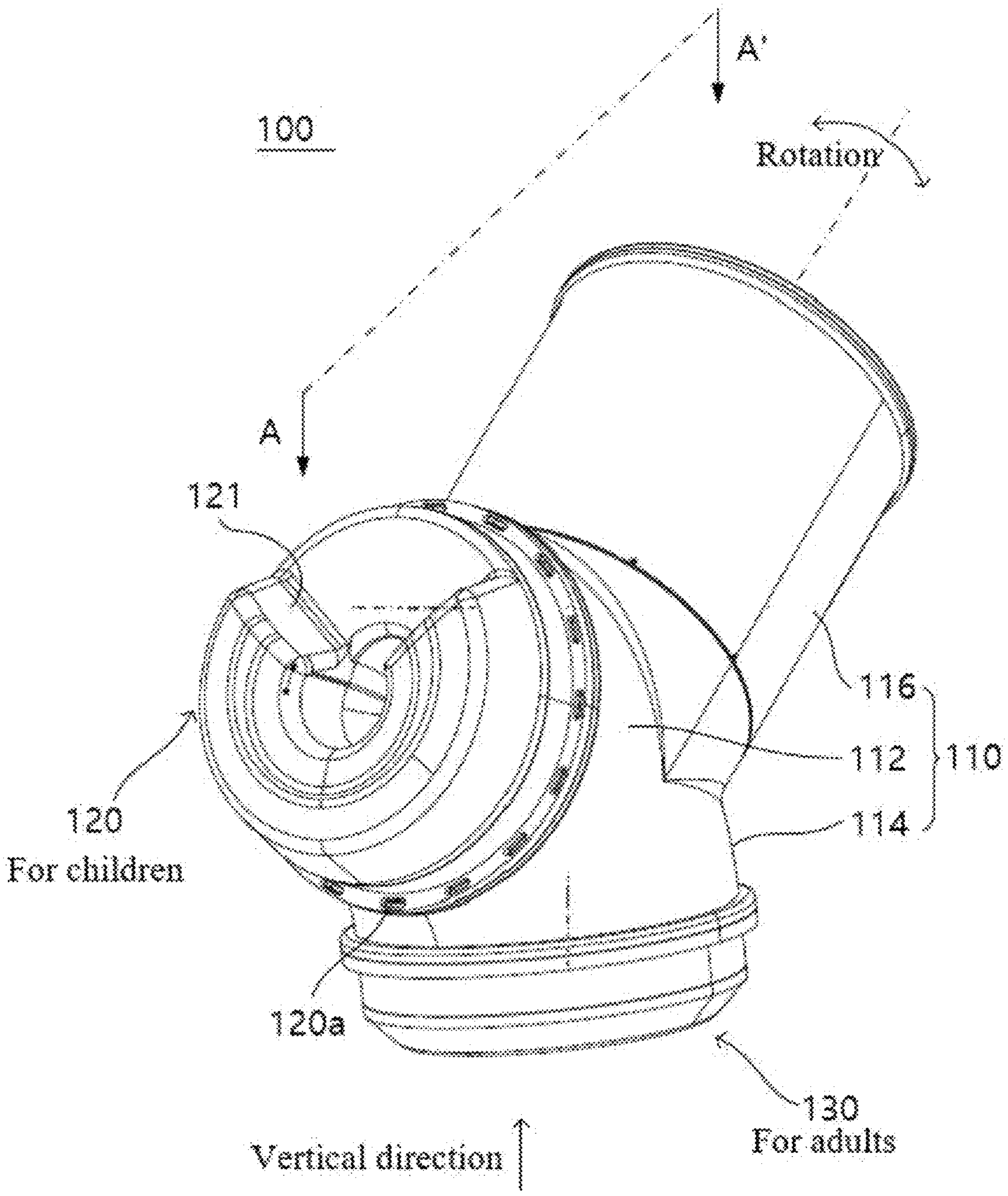
FIG. 5 is a perspective view of a magnetoencephalography measuring apparatus according to an example embodiment of the present disclosure.

FIG. 5 is a perspective view of a magnetoencephalography measuring apparatus according to an example embodiment of the present disclosure.

Figure 6A:
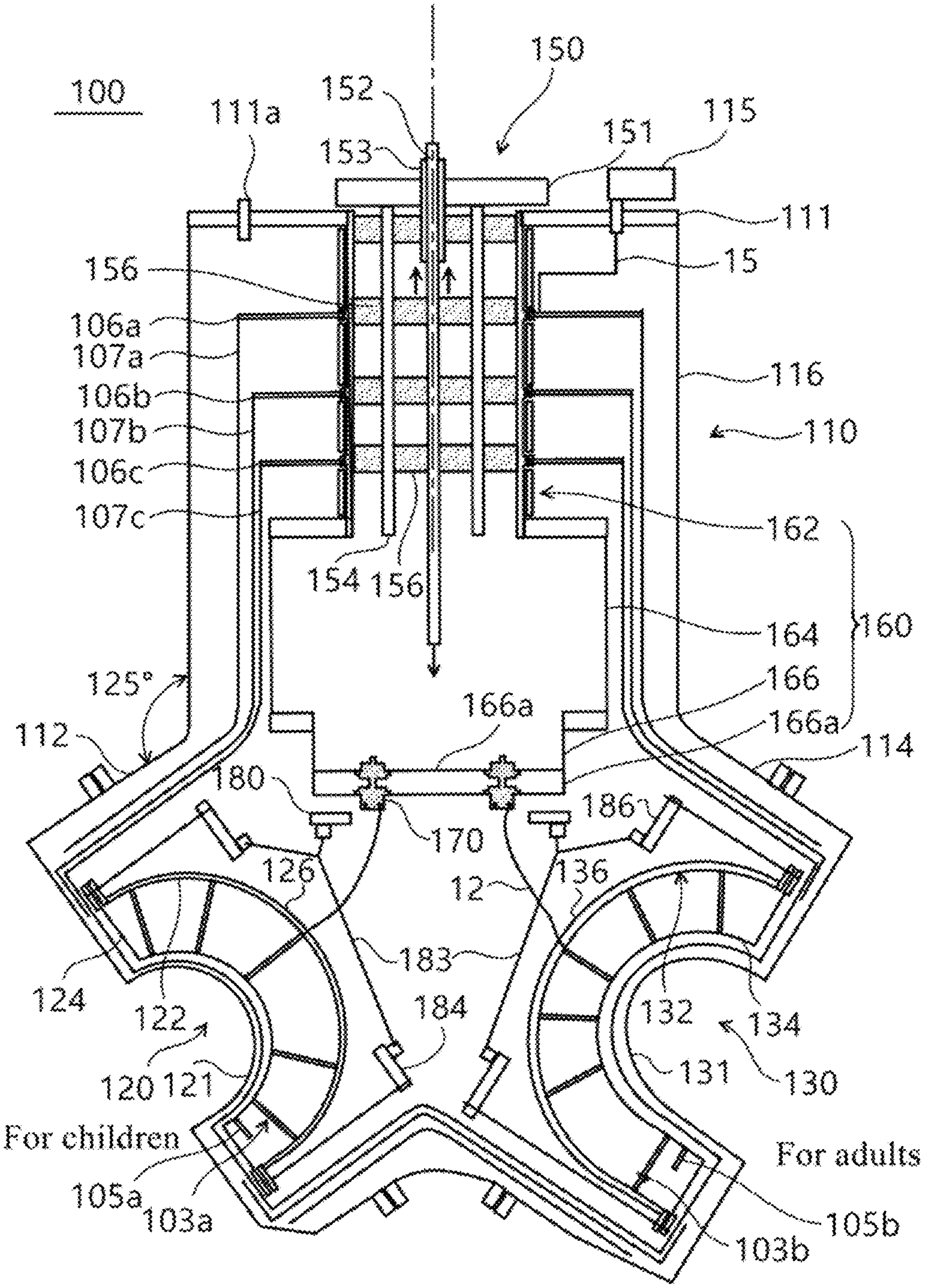
FIGS. 6A and 6B are cross-sectional views taken along line A-A' in FIG. 5.
Figure 6B:
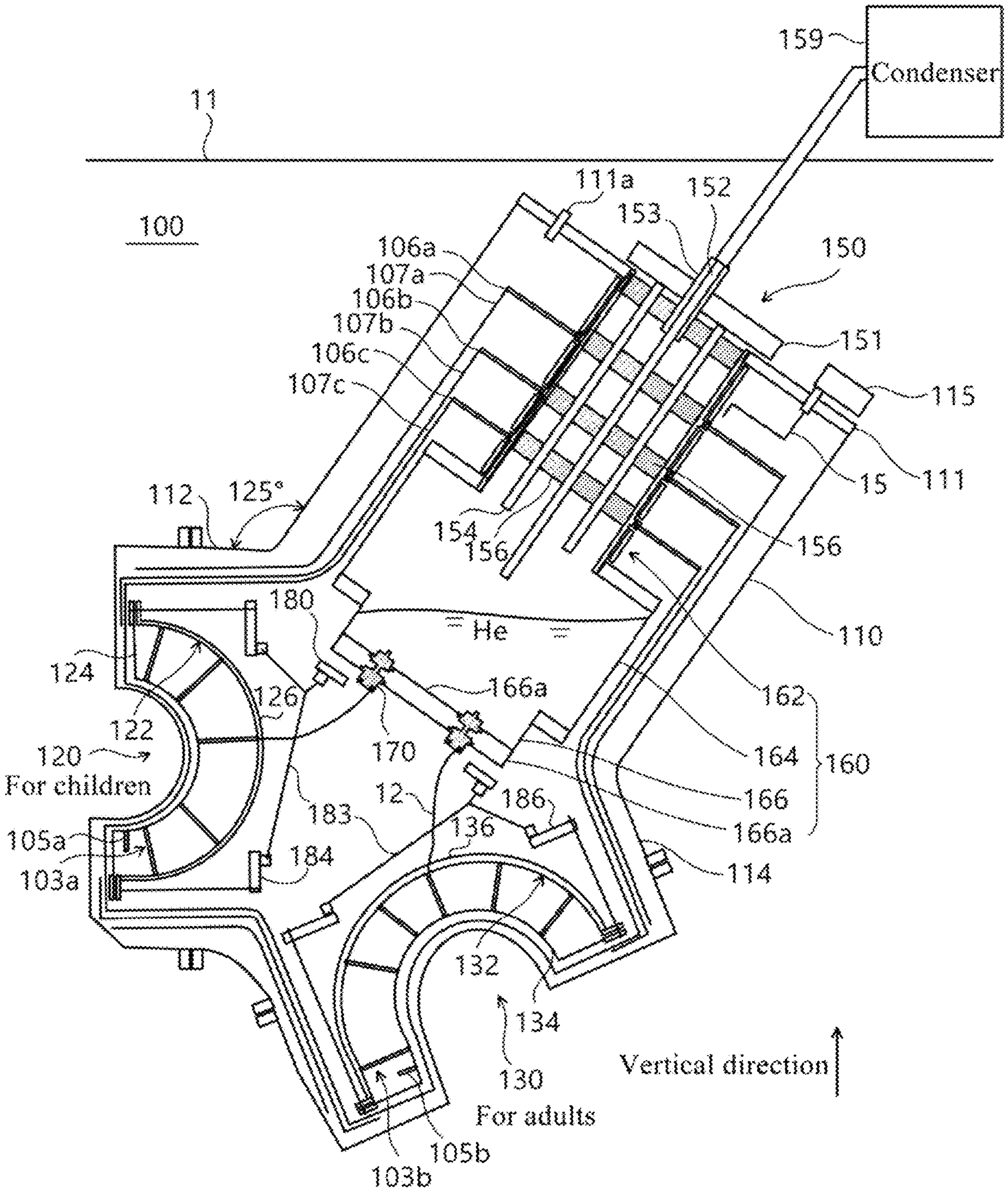

FIGS. 6A and 6B are cross-sectional views taken along line A-A' in FIG. 5.

Figure 7:
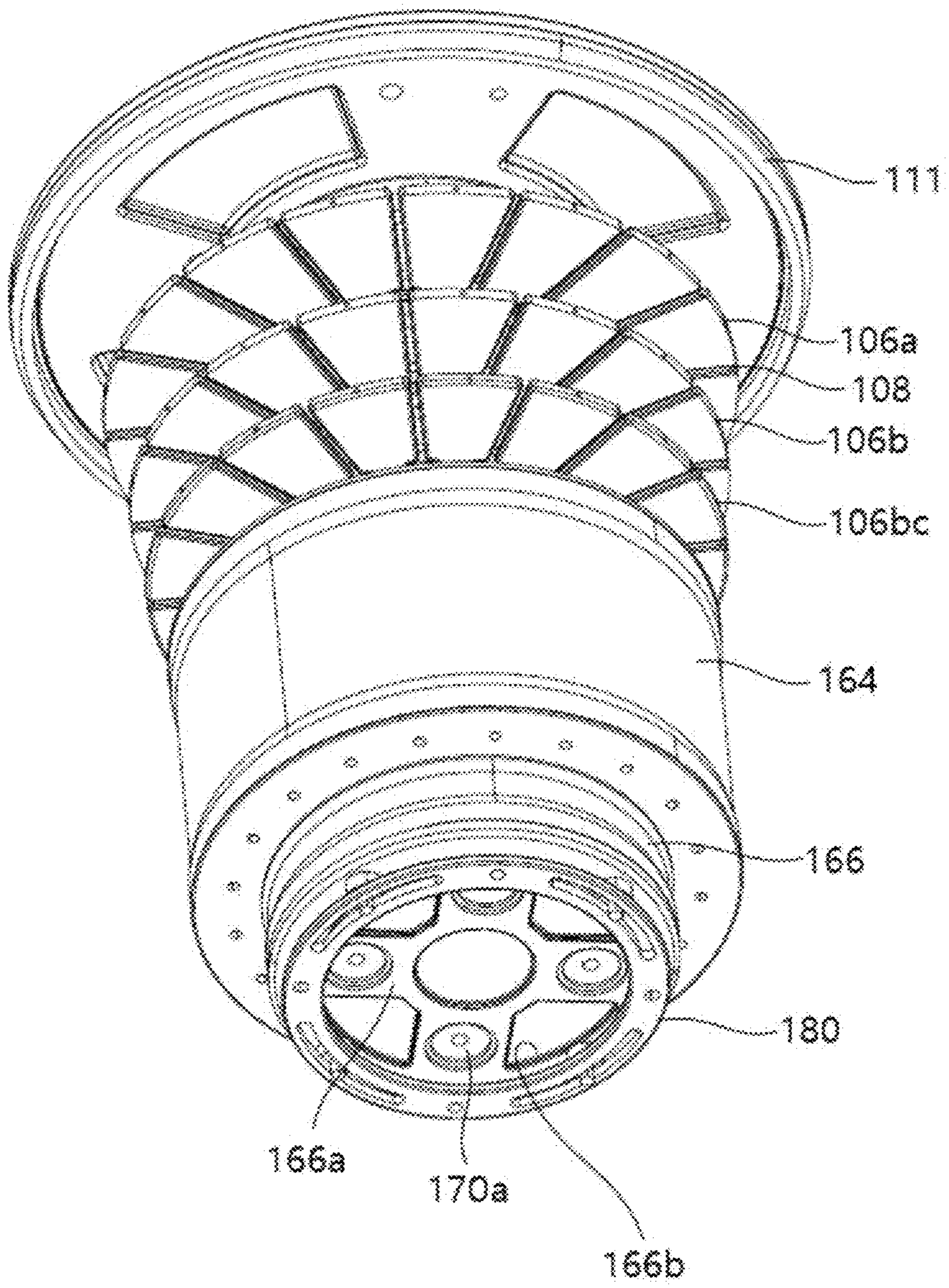
FIG. 7 is a perspective view illustrating an internal container and thermal anchors according to an example embodiment of the present disclosure.

FIG. 7 is a perspective view illustrating an internal container and thermal anchors according to an example embodiment of the present disclosure.

Figure 8:
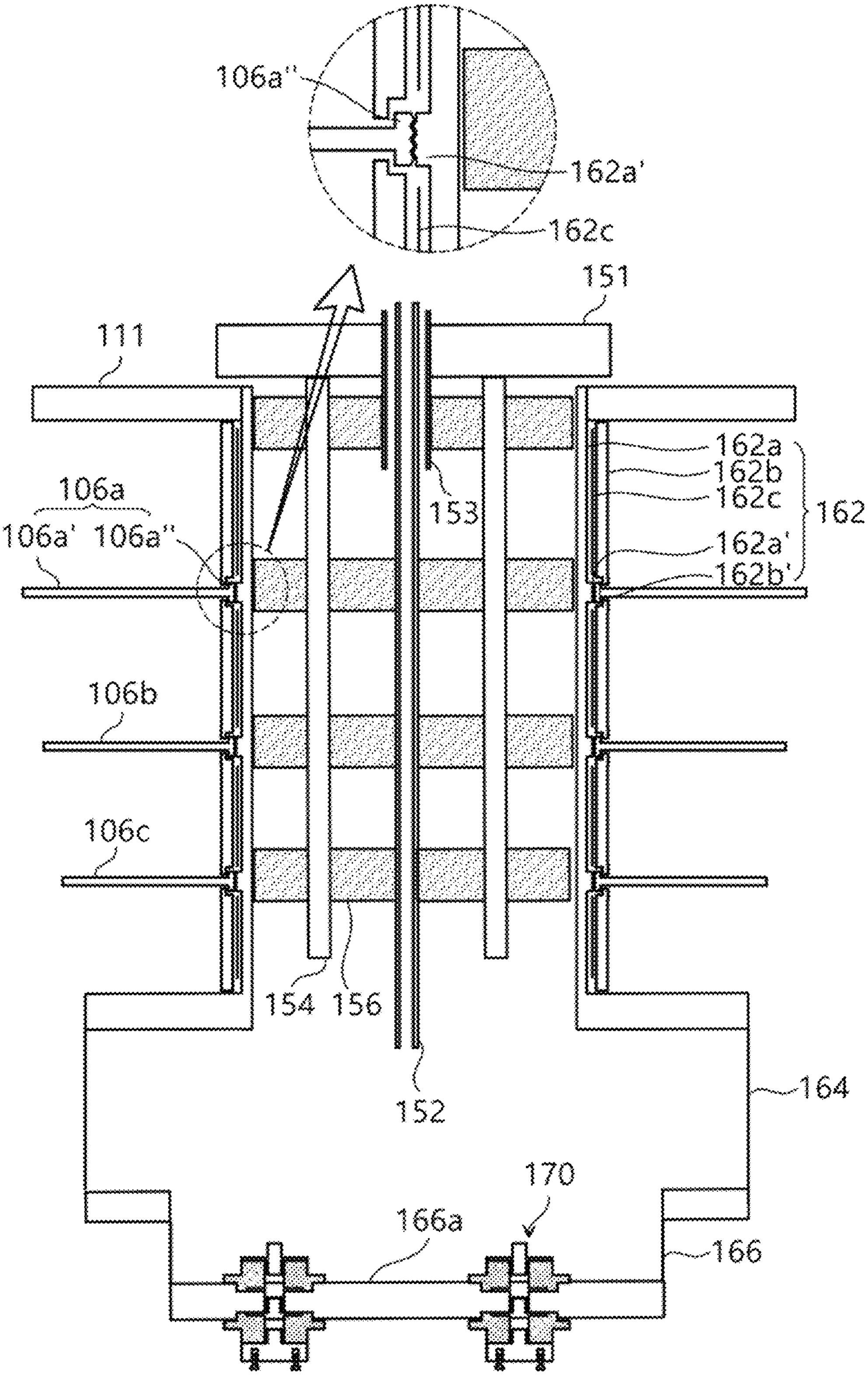
FIG. 8 is a cross-sectional view illustrating an internal container and thermal anchors according to an example embodiment of the present disclosure.

FIG. 8 is a cross-sectional view illustrating an internal container and thermal anchors according to an example embodiment of the present disclosure.

Figure 9:
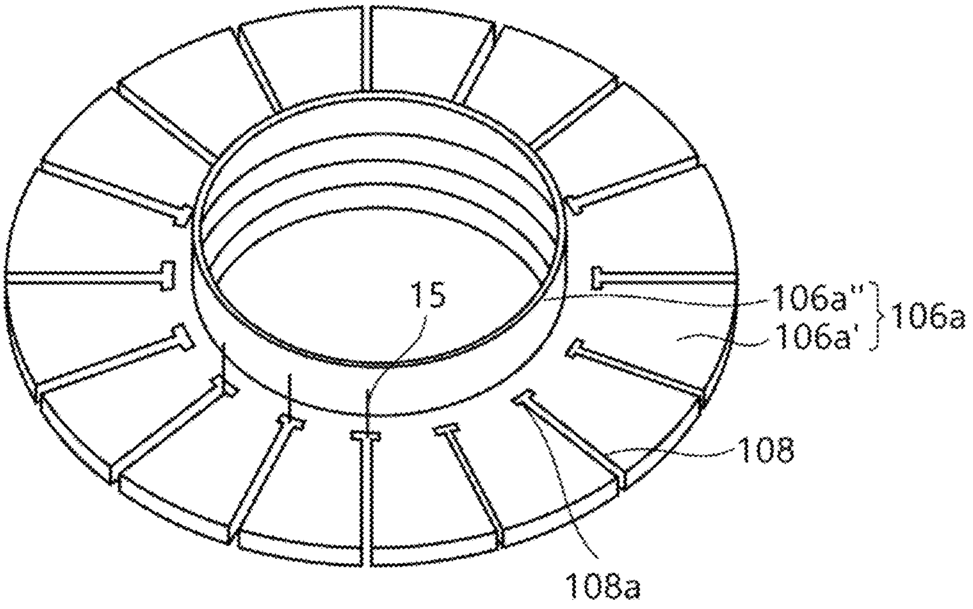
FIG. 9 is a perspective view illustrating a thermal anchor according to an example embodiment of the present disclosure.

FIG. 9 is a perspective view illustrating a thermal anchor according to an example embodiment of the present disclosure.

Referring to FIGS. 5, 6A and 6B, and 7 to 9, a magnetoencephalography measuring apparatus 100 may include an internal container 160 storing a liquid refrigerant, an external container 110 disposed to surround the internal container 160 and including a first external helmet 120 and a second external helmet 130 disposed to be spaced apart from each other, a first sensor-mounted helmet 122 disposed between the external container 110 and the internal container 160 to surround the first external helmet 120, a second sensor-mounted helmet 132 disposed between the external container 110 and the internal container 160 to surround the second external helmet 130; a plurality of first SQUID sensor modules 103*a* disposed on the first sensor-mounted helmet 122; and a plurality of second SQUID sensor modules 103*b* disposed on the second sensor-mounted helmet 132.

Each of the plurality of first SQUID sensor modules 103*a* is in thermal contact with a main thermal anchor 170, disposed on a lower surface of the internal container 160, through a litz wire 12. Each of the plurality of second SQUID sensor modules 103*b* is in thermal contact with the main thermal anchor 170, disposed on the lower surface of the internal container 160, through a litz wire 12. A space between the external container 110 and the internal container 160 is in a vacuum state. The SQUID sensors of the first sensor-mounted helmet 122 and the second sensor-mounted helmet 132 may be efficiently cooled through the litz wires 12.

The magnetoencephalography measuring apparatus 100 may be disposed inside a magnetically shielded room 11.

The external container 110 may include an external container lid 111. The external container 110 may include a first branch 112 and a second branch 114 branching off from a cylindrical external container body portion 116 in the form of Y. The first external helmet 120 and the second external helmet 130 may be coupled to the first branch 112 and the second branch 114, respectively. The first external helmet 120 may be a helmet for children, and the second external helmet 130 may be a helmet for adults. One of the first external helmet 120 and the second external helmet 130 may be parallel to measure a lying person. The other of the first external helmet 120 and the second external helmet 130 may be tilted at an angle of 20 degrees in the vertical direction to measure a sitting person.

The external container body portion 116 may be disposed to be titled at an angle of 30 degrees to 45 degrees in a vertical direction. The first external helmet 120 and the second external helmet 130 may be disposed to be spaced apart from each other at an interval of 110, based on central axes thereof. The internal container 160 and the external container 110 may be titled at an angle of 30 degrees to 45 degrees in the vertical direction. The internal container 160 and the external container 110 may be tilted at an angle of 35 degrees in the vertical direction. Accordingly, the refrigerant stored in the internal container 160 may also be tilted.

The external container body portion 116 may rotate about a central axis thereof. The first external helmet 120 may be applied to a subject in a sitting state or a lying state depending on a rotational state of the external container 110.

The magnetoencephalography measuring apparatus 100 may further include a rotational motion unit (not illustrated) coupled to the outside of the external container body portion 116. The rotational motion unit may include a bearing formed of a non-conductive material. The rotational motion unit 140 may be fixed to a ceiling of a magnetically shielded room 11 through an external support (not illustrated), or may be fixed to an additional support (not illustrated) mounted in the magnetically shielded room 11.

The first external helmet 120 may have a long groove 120*a* in a coupling portion coupled to the first branch 112. The first external helmet 120 may rotate along the long groove 120*a* to be coupled to one end of the first branch 112 while being aligned with the first branch 112. The long groove 120*a* may provide an alignment between the first external helmet 120 and the first sensor-mounted helmet 122.

The second external helmet 130 may have a long groove in a coupling portion coupled to the second branch 114. The second external helmet 130 may rotate along the long groove to be coupled to one end of the second branch 114 while being aligned therewith.

The internal container 160 may store a liquid refrigerant, and may cool a SQUID sensor module through a main thermal anchor and a litz wire.

The internal container 160 may include a neck portion 162 into which the baffle insert 150 is inserted, an upper body portion 164 having an increased diameter as compared with the neck portion 162, and a lower body portion 166 having a deceased diameter as compared with the upper body portion 164.

The neck portion 162 may have a double-wall structure including an internal cylinder and an external cylinder surrounding the internal cylinder. The upper body portion 164 may be continuously connected to the neck portion 162. The lower body portion 166 may be continuously connected to the upper body portion 164. The diameter of the lower body portion 166 may be smaller than the diameter of the upper body portion 164. The lower body portion 166 may provide efficient cooling of the SQUID sensor by decreasing a distance between the first sensor-mounted helmet 122 and the second sensor-mounted helmet 132. A lower surface of the lower body portion 166 may be lower than a position in which the external container 110 branches off in the form of Y.

A lower surface 166*a* of the lower body portion 166 may include a plurality of fan-shaped getter grooves 166*b* in a direction toward a vacuum side. A getter for trapping residual gas may be disposed in the getter groove.

The neck portion 162 may include an internal cylinder 162*a* and an external cylinder 162*b* surrounding the internal cylinder 162*a*. A heat shielding layer 162*c* may be disposed between the internal cylinder 162*a* and the external cylinder 162*b*. The heat shielding layer 162*c* may be a metal mesh woven with metal wires insulated from each other.

The internal cylinder 162*a* may further include a plurality of ring projections 162*a*' protruding outwardly of a cylinder. The ring projection 162*a*' has a cylindrical ring shape, and may be formed to be integrated with the internal cylinder 162*a*. A screw for screw-coupling may be formed on an external circumferential surface of the ring projection 162*a*'.

The ring projections 162*a*' may be disposed to be spaced apart from each other. The external cylinder 162*b* may be divided with the ring projection 162*a*' interposed therebetween. That is, the external cylinder 162*b* may include a plurality of cylindrical portions separated from each other. A distance between the external cylinder 162*b* and the internal cylinder 162*a* may be within several millimeters (mm). Each of the external cylinders 162*a* may include a thermal anchor coupling portion 106*a*" and a raised portion 162*b*' to surround the ring projection 162*a*'. After the external cylinder 162*b* is coupled to surround the ring projection 162*a*', a coupling portion may be fixed and sealed with an adhesive such as epoxy.

The thermal anchors 106a, 106b, and 106c may be coupled to the ring projections 162a', respectively. An external circumferential surface of the ring projection 162a' and internal circumferential surfaces of the thermal anchors 106a, 106b, and 106c may be screw-coupled. Each of the thermal anchors 106a, 106b, and 106c may have a circular washer shape. The thermal anchors 106a, 106b, and 106c may be copper or aluminum.

The thermal anchor 106a may include a cylindrical thermal anchor coupling portion 106a" and a disc-shaped thermal anchor body 106a' disposed on an external circumferential surface of the coupling portion. An internal circumferential surface of the thermal anchor coupling portion 106a" may be screw-coupled to an internal circumferential surface of the ring projection.

The screw connection of the ring projection 162a' and the thermal anchor 106a may improve mechanical stability while providing efficient thermal contact brought by thermal expansion.

The double-wall structure may block radiant heat influx into the internal container 160 from the outside. When the internal container 160 is cooled by a refrigerant, a space between the internal cylinder 162a and the external cylinder 162b may be maintained in a vacuum state. Accordingly, heat influx caused by heat transfer may be blocked and the heat shielding layer 162c may additionally block radiant heat influx. As a result, the neck portion of the double-wall structure may provide high mechanical stability and high heat shielding efficiency, as compared with a neck portion of a single-wall structure.

The thermal anchors 106a, 106b, and 106c may include first to third thermal anchors 106a, 106b, and 106c disposed in order. The first thermal anchor 106a may be disposed on an uppermost side of the neck portion 162, and may be connected to a 120K heat shielding layer 107a. The second thermal anchor 106b may be disposed below the first thermal anchor 106a, and may be connected to an 80K heat shielding layer 107b. The third thermal anchor 106c may be disposed below the second thermal anchor 106b, and may be connected to a 40K heat shielding layer 107c.

The first thermal anchor 106a may farthest spaced apart from the refrigerant to be maintained at a highest temperature, and the third thermal anchor 106c may be closest to the refrigerant to be maintained at a lowest temperature. The first to third thermal anchors 106a, 106b, and 106c may be in thermal contact with an evaporated refrigerant to be cooled.

Each of the first to third row anchors 106a, 106b, and 106c may include a plurality of slits 108 extending in a radial direction. The slit 108 may provide a path through which signal lines 15 of SQUID sensors pass. The signal lines 15 may be gathered in the groove 108a of the slit 108 to be connected to a signal line connection box 115 disposed on an external container lid 111.

The 40K heat shielding layer 107c may be coupled to an external circumferential surface of the third thermal anchor 106c, and may be disposed to surround the internal container 160 and to block radiant heat influx. The 40K heat shielding layer 107c may include a metal mesh, woven with metal wires insulated from each other, and a heat insulation film. The 40K heat shielding layer 107c may branch off in the form of pants to surround the first sensor-mounted helmet 122 and the second sensor-mounted helmet 132, and then may surround the first sensor-mounted helmet 122 and the second sensor-mounted helmet 133.

The 80K heat shielding layer 107b may be coupled to an external circumferential surface of the second thermal anchor 106b, and may be disposed to surround the 40K heat shielding layer 107c and to block the radiant heat influx. The 80K heat shielding layer 107b may include a metal mesh, woven with metal wires insulated from each other, and a heat insulation film. The 80K heat shield 107b may be branched into a pants shape to surround the first sensor-mounted helmet 122 and the second sensor-mounted helmet 132. The 80K heat shielding layer 107b may extend in a brim direction of the first sensor-mounted helmet 122, and may extend in a brim direction of the second sensor-mounted helmet 132.

The 120K heat shielding layer 107a may be coupled to an external circumferential surface of the first thermal anchor 106a, and may be disposed to surround the 80K heat shielding layer 107b and to block the radiant heat influx. The 120K heat shielding layer 107a may include a metal mesh, woven with metal wires insulated from each other, and a heat insulation film. The 120K heat shielding layer 107a may branch off in the form of pants to surround the first sensor-mounted helmet 122 and the second sensor-mounted helmet 132.

A space between the internal container 160 and the external container 110 may be maintained in a vacuum state. The external container lid 111 may include an exhaust port 111a, connected to a vacuum pump, and a signal port connecting a signal line to an external entity. The exhaust port may be formed of a G-10 epoxy tube.

The baffle insert 150 may be disposed to be inserted into the neck 162 of the internal container 160. The baffle insert 150 may include an insert upper plate 151, a baffle 156 disposed below the insert upper plate 151, and a plurality of guide rods 154 supporting the baffle 156 and fixed to the insert upper plate 151.

The insert upper plate 151 may have a disc shape, and may be formed of G-10 epoxy. The insert upper plate 151 may be fixed to the external container lid 111. The guide rod 154 is formed of G-10 epoxy, and may have a rod shape or a pipe shape. The guide rod 154 may support the baffle 156. The baffle 156 may include Styrofoam having improved warmth retention and a conductive plate. The conductive plate may include an aluminum-coated Mylar layer and a copper layer sequentially stacked to block the radiant heat.

A refrigerant exhaust tube 153 may be disposed on the insert upper plate 151 of the baffle insert 150, and may exhaust an evaporated refrigerant. The refrigerant injection tube 152 may be disposed on the insert upper plate 151 of the baffle insert 150, and may inject a refrigerant. Each of the refrigerant exhaust tube 153 and the refrigerant injection tube 152 may be a dual tube including an internal tube and an external tube. In the dual tube, a space between the internal tube and the external tube may be maintained in a vacuum state during cooling. The refrigerant injection tube 152 may have a coaxial structure inserted into the refrigerant exhaust tube 153. The refrigerant exhaust tube 153 and the refrigerant injection tube 152 may be formed of G-10 epoxy.

The coaxial dual tube may reduce a thermal contact with the insert upper plate 151 to reduce ice formation in the insert upper plate 151. When the refrigerant exhaust tube 153 and the refrigerant injection tube 152 are a single tube, the insert upper plate 151 and the refrigerant exhaust tube 153 may form ice, and the ice may inhibit sealing of the external container lid 111 and the insert upper plate 151 and may increase heat influx from the outside.

The condenser 159 may be connected to the refrigerant exhaust tube 153 and the refrigerant injection tube 152, and may condense the evaporated refrigerant exhausted through the refrigerant injection tube 152 and may transfer the condensed refrigerant to the internal container 160 through the refrigerant injection tube 152. The condenser 159 may be disposed outside the magnetically shielded room 11.

Figure 10:
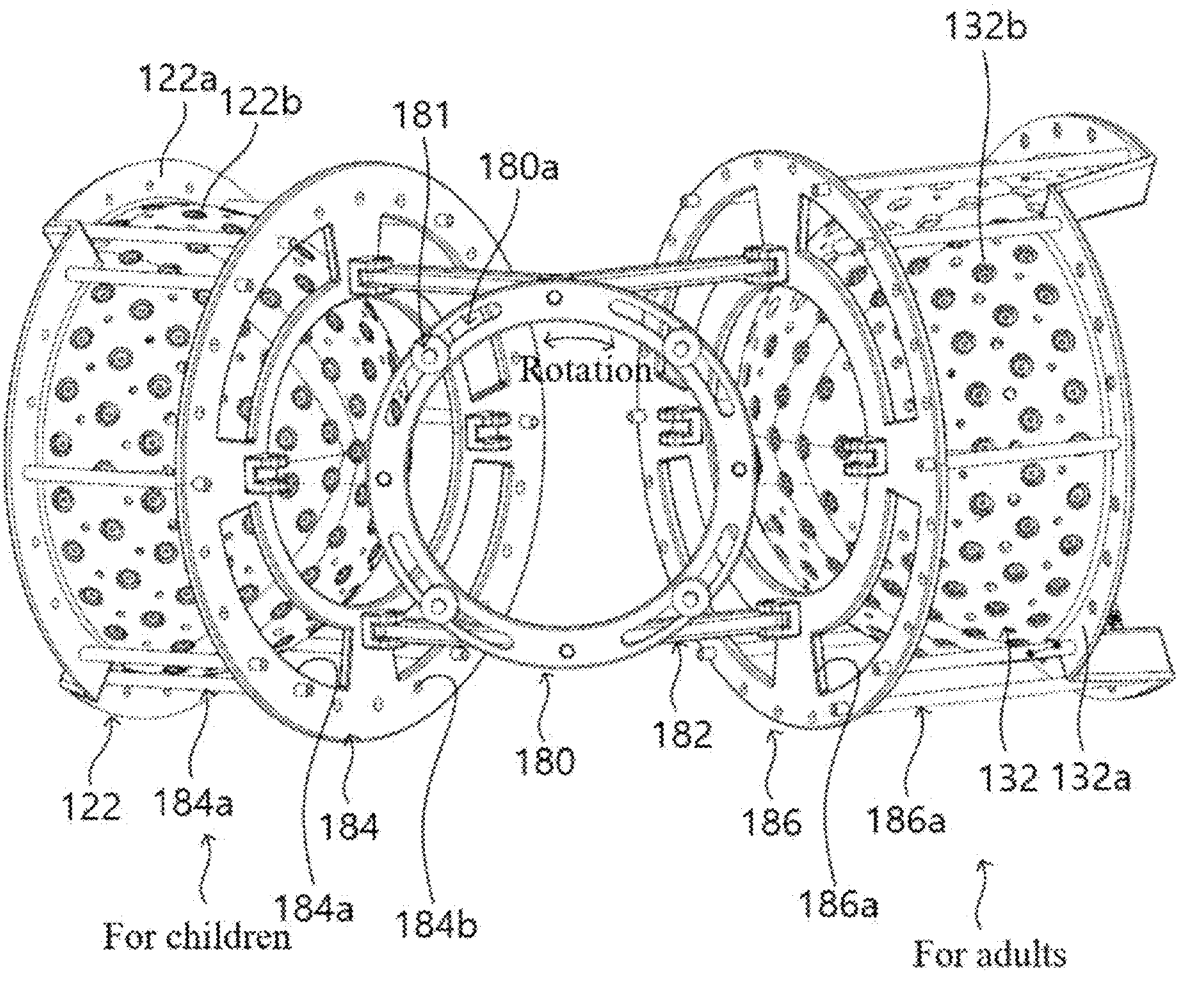
FIG. 10 is a perspective view illustrating a first sensor-mounted helmet and a second sensor-mounted helmet according to an example embodiment of the present disclosure.

FIG. 10 is a perspective view illustrating a first sensor-mounted helmet and a second sensor-mounted helmet according to an example embodiment of the present disclosure.

Figure 11:
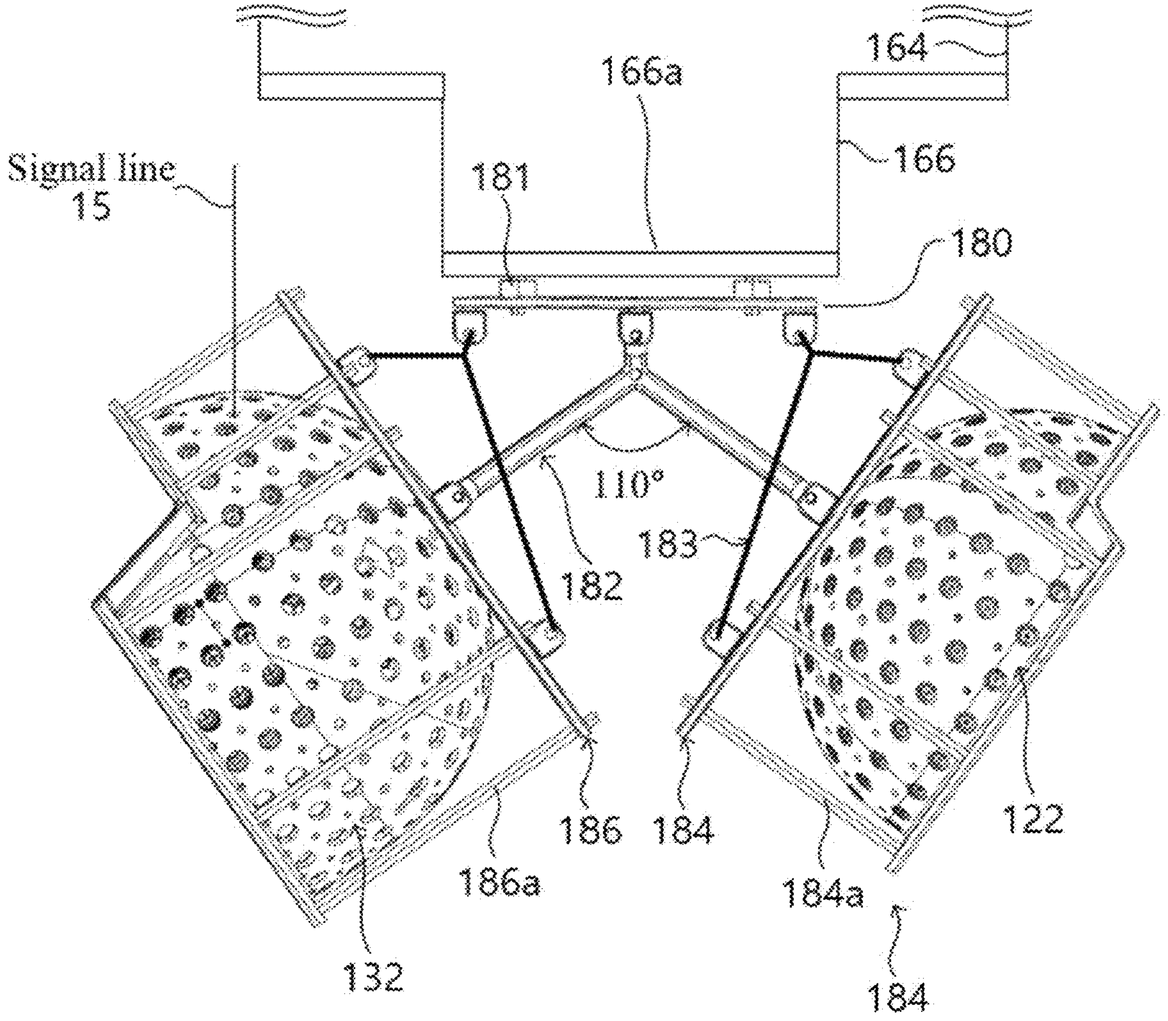
FIG. 11 is a front view of the first sensor-mounted helmet and the second sensor-mounted helmet in FIG. 10.

FIG. 11 is a front view of the first sensor-mounted helmet and the second sensor-mounted helmet in FIG. 10.

Referring to FIGS. 10 and 11, a first sensor-mounted helmet 122 may be configured to cover the head, and may include an open portion to secure a subject's view. The first sensor-mounted helmet 122 may include a brim **122*a* on an edge thereof. The brim 122*a* may be connected to a fixing means for fixing the first sensor-mounted helmet 122**.

A second sensor-mounted helmet 132 is configured to cover a head, and may include an open portion to secure a subject's view. The second sensor-mounted helmet 132 may include a brim **132*a* on an edge thereof. The brim 132*a* may be connected to a fixing means for fixing the second sensor-mounted helmet 132**.

A first fixing ring 184 may be disposed to be vertically spaced apart from the first sensor-mounted helmet 122, and may have a washer shape. A plurality of first support pillars **184*a* may connect the first fixing ring 184 and the brim 122*a* of the first sensor-mounted helmet 122 to each other. The first fixing ring 184 includes a plurality of arc openings 184*a* and through-holes 184*b*. The arc opening 184*a* may prevent litz wires for cooling a SQUID sensor module form being twisted. In addition, the through-holes 184*b* may provide a passage of litz wires for cooling the first auxiliary thermal anchor 185**.

A second fixing ring 186 may be disposed to be vertically spaced apart from the second sensor-mounted helmet 132, and may have a washer shape. A plurality of second support pillars **186*a* may connect the second fixing ring 186 and the brim 132*a* of the second sensor-mounted helmet 132 to each other. The second fixing ring 186 may include a plurality of arc openings 186*a* and through-holes 186*b*. The arc opening 186*a* may prevent litz wires for cooling the SQUID sensor module from being twisted. In addition, the through-holes 186*b* may provide a passage for litz wires for cooling the first auxiliary thermal anchor 185**.

A helmet alignment support portion 180 may be disposed to be spaced apart from a lower surface **166*a* of the internal container 160. A central axis of the helmet alignment support portion 180 may be spaced apart from a central axis of the first fixing ring 184 at an angle of 125 degrees. The central axis of the helmet alignment support portion 180 may be spaced apart from a central axis of the second fixing ring 186 at an angle of 125 degrees. The central axis of the first fixing ring 184 and the central axis of the second fixing ring 186** may be spaced apart from each other at angle of 110 degrees.

The helmet alignment support portion 180 may have a ring shape, and may include a plurality of curved long grooves **180*a***.

A coupling member 181 may be inserted into each of the curved long grooves **180*a*, and may be coupled to a lower surface 166*a* of the internal container 160. The curved long grooves 180*a* may align the first sensor-mounted helmet 122 and the second sensor-mounted helmet 132 with the first external helmet 120 and the second external helmet 130**.

A plurality of fixing ring support portions 182 and 183 may fix the first fixing ring 184 and the second fixing ring 186 to the helmet alignment support portion 180.

Each of the pair of first fixing ring support parts 182 may have a Y shape, and may connect the first fixing ring 184 and the second fixing ring 186 to each other and may be fixed to the helmet alignment support portion 180. The second fixing ring support portion 183 may have an L shape, and may be connected to two points of the first fixing ring 184 and may be fixed to the helmet alignment support portion 180. In addition, the second fixing ring support portion 183 may have an L shape, and may be connected to two points of the second fixing ring 186 and may be fixed to the helmet alignment support portion 180.

Figure 12:
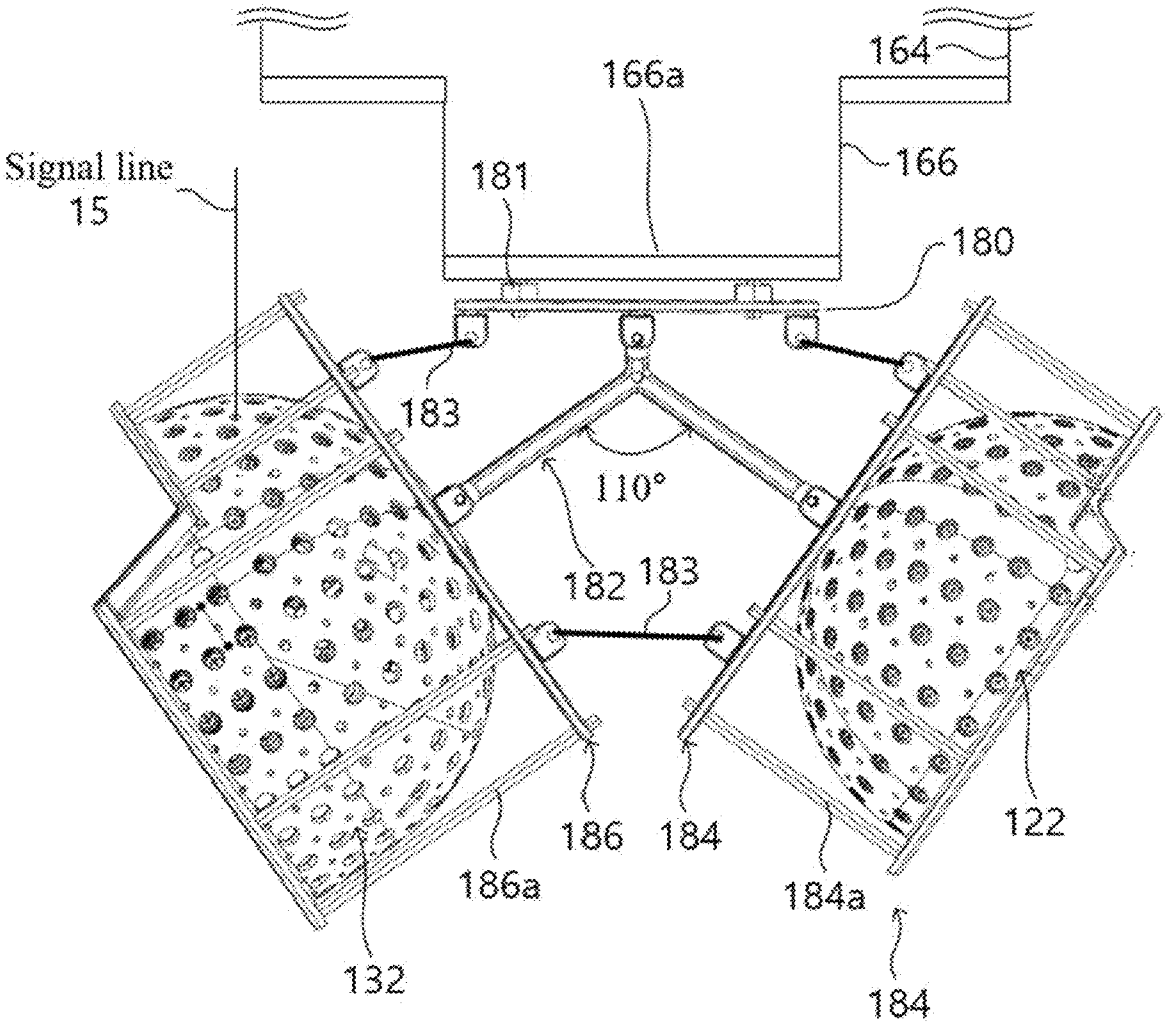
FIG. 12 is a front view of a perspective view of a first sensor-mounted helmet and a second sensor-mounted helmet according to another example embodiment of the present disclosure.

FIG. 12 is a front view of a perspective view of a first sensor-mounted helmet and a second sensor-mounted helmet according to another example embodiment of the present disclosure.

Referring to FIG. 12, each of a pair of first fixing ring support portion 182 may have a Y shape, and may connect a first fixing ring 184 and a second fixing ring 186 to each other and may be fixed to a helmet alignment support 180. A second fixing ring support portion 183 may have a linear shape, and may connect the first fixing ring 184 and the second fixing ring 186 to each other. The second fixing ring support portion 183 may connect a point of the first fixing ring 184 and the helmet alignment support portion 180 to each other. The second fixing ring support portion 183 may connect a point of the second fixing ring 186 and the helmet alignment support portion 180 to each other.

Figure 13:
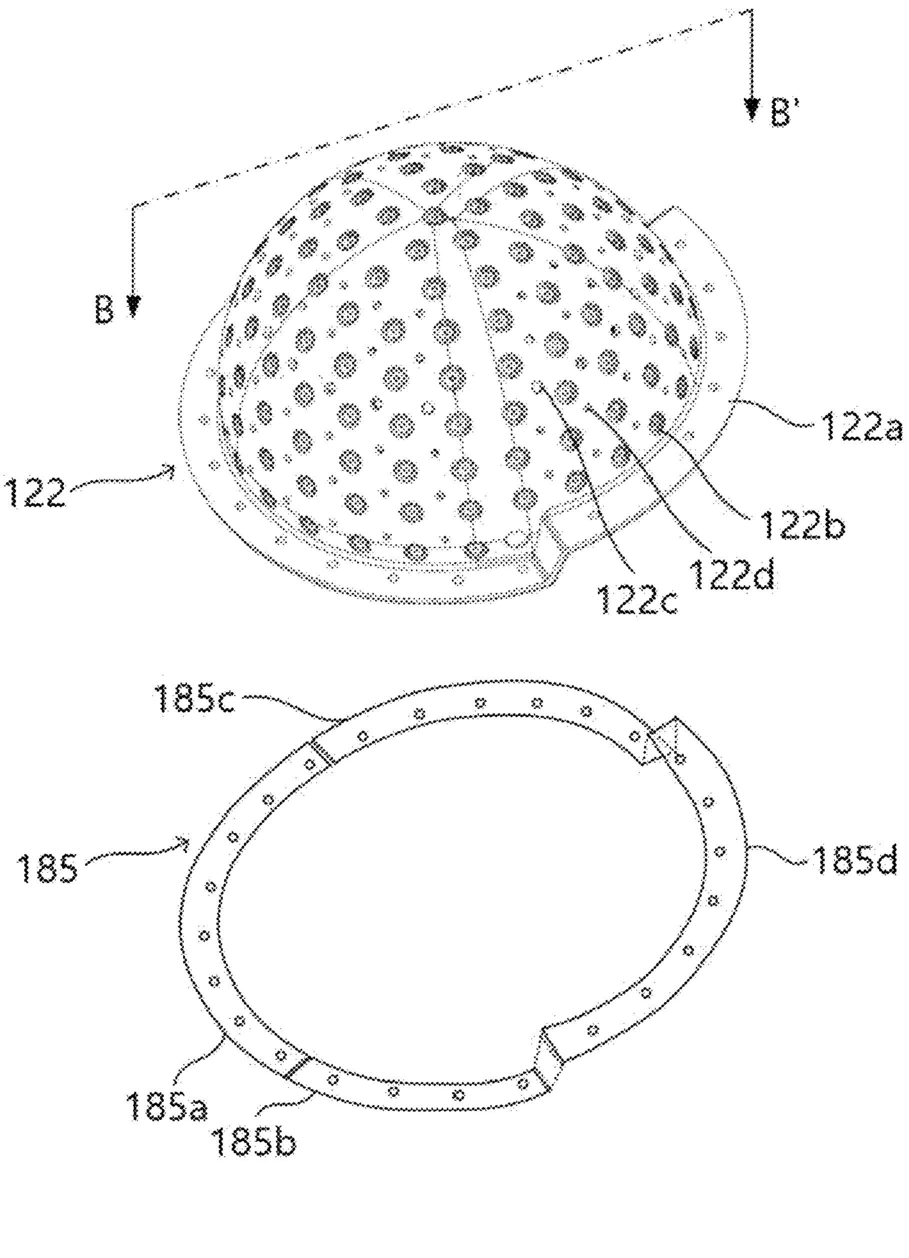
FIG. 13 is a perspective view illustrating a sensor-mounted helmet according to an example embodiment of the present disclosure.

FIG. 13 is a perspective view illustrating a sensor-mounted helmet according to an example embodiment of the present disclosure.

Figure 14:
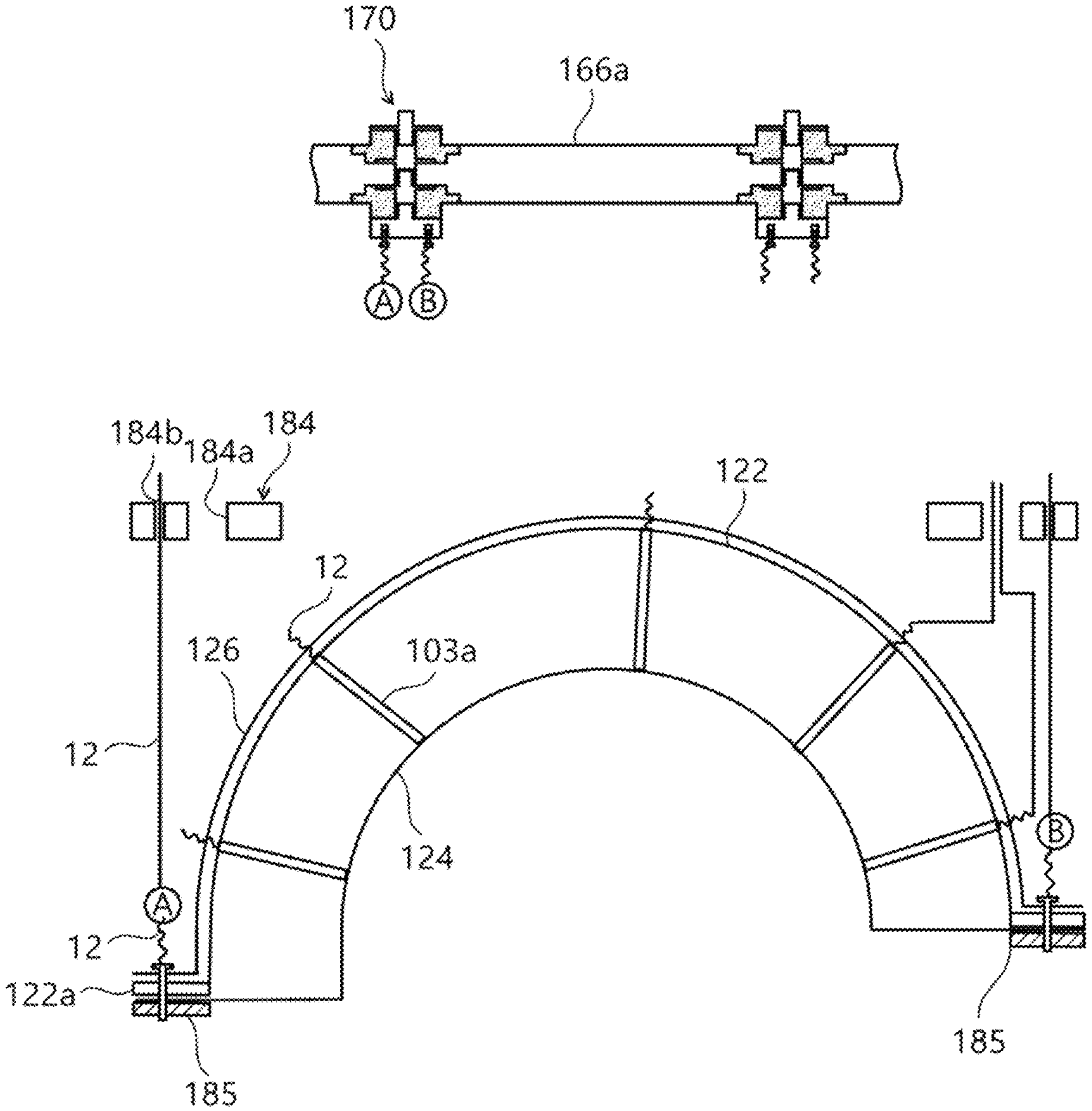
FIG. 14 is a cross-sectional view taken along line B-B' in FIG. 13.

FIG. 14 is a cross-sectional view taken along line B-B' in FIG. 13.

Referring to FIGS. 13 and 14, a first sensor-mounted helmet 122 may include a brim **122*a* on an edge thereof. The first sensor-mounted helmet 122 may have the same structure as a second sensor-mounted helmet 132, but may be different from the second sensor-mounted helmet 132 in size and the number of SQUID sensor modules. The first sensor-mounted helmet 122 may have a first through-hole 122*b* for mounting a SQUID sensor module, a second through-hole 122*c* for placing a signal line, and a third through-hole 122*d* for mounting a fixing member for fixing a SQUID sensor module 103*a*. Signal lines, respectively connected to the SQUID sensor modules 103*a*, may be gathered and disposed along the groove 108*a*, connected to a slit 180 of a thermal anchor, through the second through-hole 122*c***.

A first auxiliary thermal anchor 185 may be disposed on a lower surface of the brim **122*a* of the first sensor-mounted helmet 122. The first auxiliary thermal anchor 185 may be divided into a plurality of components 185*a* to 185*d*. The first auxiliary thermal anchor 185 may be formed of an oxygen-free copper strip. The first auxiliary thermal anchor 185 may be divided to reduce eddy current noise and thermal noise caused by a high frequency, and may provide a uniform temperature gradient depending on a location. The first auxiliary thermal anchor 185 may be in thermal contact with a main thermal anchor 170 through a litz wire 12**.

A first internal 4K heat shielding portion 124 may be in thermal contact with the first auxiliary thermal anchor 185, and may be disposed on an internal side surface of the first sensor-mounted helmet 122. The first internal 4K heat shielding portion 124 may be disposed to cover the SQUID sensor modules **103*a***, and may include an insulation-coated metal mesh.

The first external 4K heat shielding portion 126 may be in thermal contact with the first auxiliary thermal anchor 185, and may be disposed on an external side surface of the first sensor-mounted helmet 122. A first external 4K heat shielding portion 126 may be disposed to cover an external surface of the first sensor-mounted helmet 122. The first external 4K heat shielding portion 126 may include an insulation-coated metal mesh. Accordingly, the first auxiliary thermal anchor 185, the first internal 4K heat shielding portion 124, and the first external 4K heat shielding portion 126 may be in thermal contact with the main thermal anchor 170 through the litz wire 12.

A second auxiliary thermal anchor may be disposed on a lower surface of the brim of the second sensor-mounted helmet 132. A second internal 4K heat shielding portion may be in thermal contact with a second auxiliary thermal anchor, and may be disposed on an internal side surface of the second sensor-mounted helmet 132. A second external 4K heat shielding portion may be in thermal contact with the second auxiliary thermal anchor, and may be disposed on an external side surface of the second sensor-mounted helmet. The second auxiliary thermal anchor, the second internal 4K heat shielding portion, and the second external 4K heat shielding portion may be in thermal contact with the main thermal anchor 170 through the litz wire 12.

Figure 15:
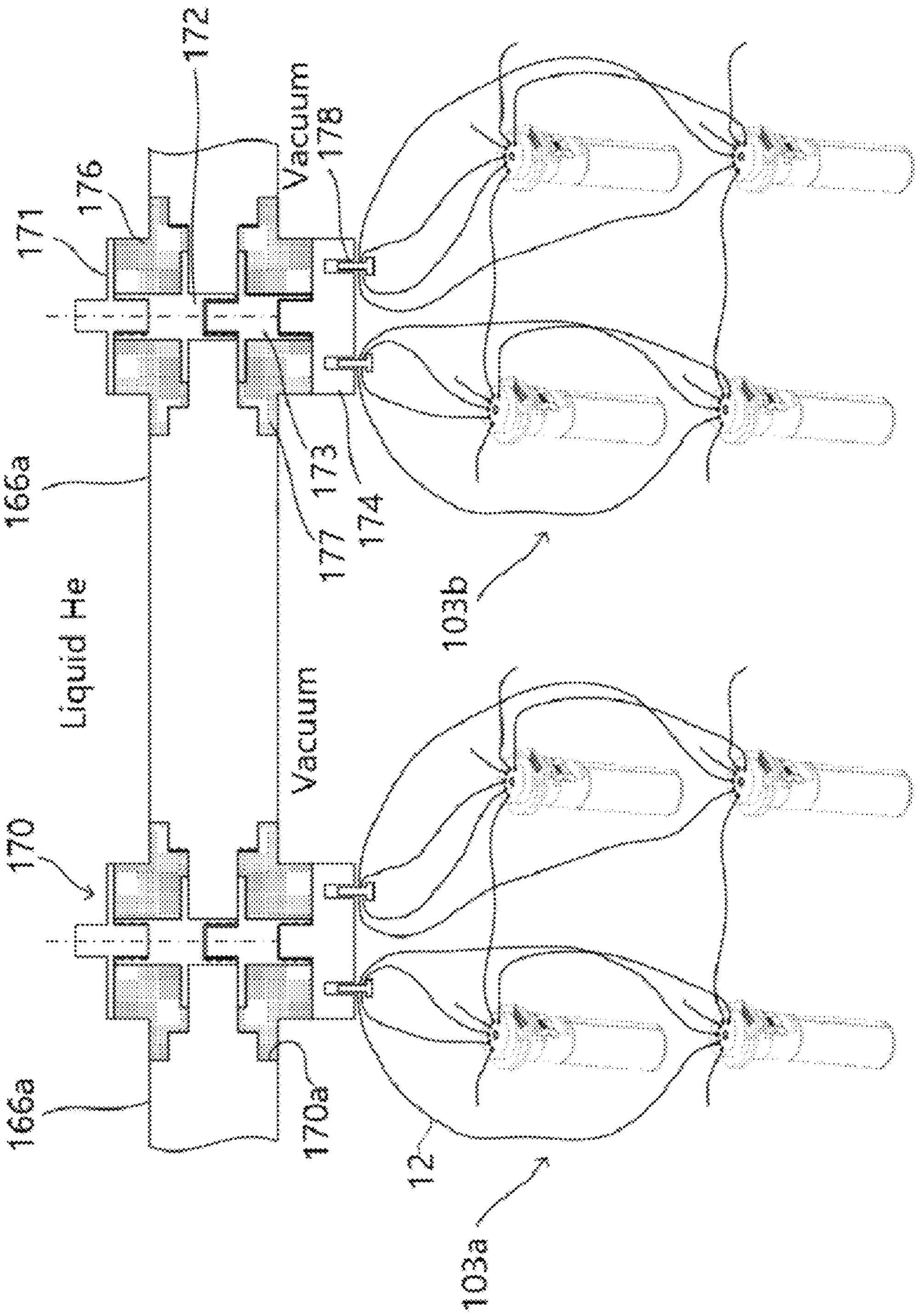
FIG. 15 is a conceptual diagram illustrating a main thermal anchor according to an example embodiment of the present disclosure.

FIG. 15 is a conceptual diagram illustrating a main thermal anchor according to an example embodiment of the present disclosure.

Figure 16:
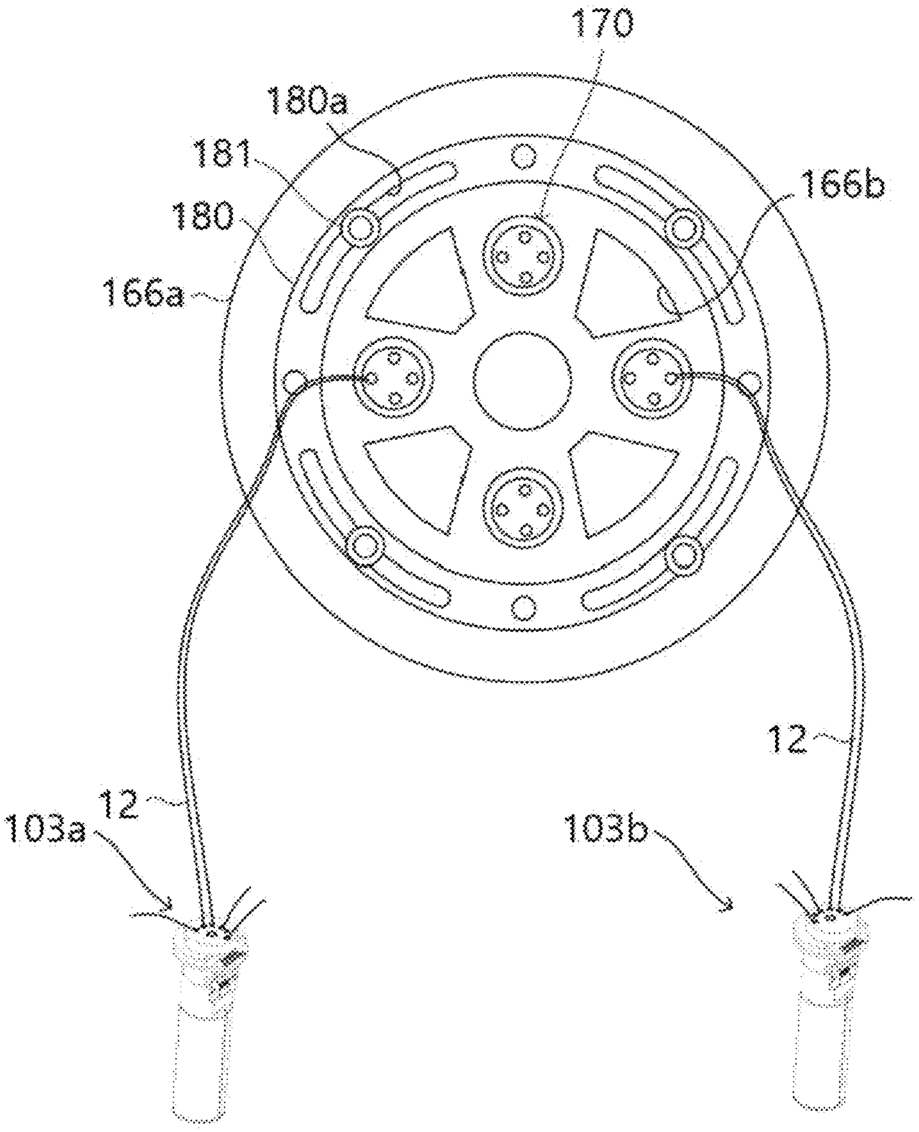
FIG. 16 is a conceptual diagram illustrating a connection relationship between a main thermal anchor and a SQUID sensor module.

FIG. 16 is a conceptual diagram illustrating a connection relationship between a main thermal anchor and a SQUID sensor module.

Referring to FIGS. 15 and 16, each of the plurality of first SQUID sensor modules 103*a* may be in thermal contact with a main thermal anchor disposed on the lower surface of the internal container 160 through a litz wire 12. Each of the plurality of second SQUID sensor modules 103*b* may be in thermal contact with the main thermal anchor 170 disposed on the lower surface of the internal container 160 through a litz wire 12.

The main thermal anchor 170 may include a first heat transfer unit 171, a second heat transfer unit 172, a third heat transfer unit 173, a fourth heat transfer unit 174, a first thermal expansion control unit 176, and a second thermal expansion control unit 177. The main thermal anchor 170 may include a plurality of components to increase a thermal contact area while inhibiting damage to the internal container 160 caused by thermal expansion, and thus, may efficiently cool the litz wire 12 and the SQUID sensor.

The first thermal expansion control unit 176 may be coupled to a dual groove having two radii formed on an internal side of the lower surface of the internal container 160, and the second thermal expansion control unit 177 may be coupled to a dual groove having two radii formed on an external side of the lower surface of the internal container 160.

The first heat transfer unit 171 may be formed of oxygen-free copper and may include a first disc 171*a*, and a first lower projection 171*b* protruding from a central axis of the first disc 171*a* to a lower surface of the first disc 171*a*. The first heat transfer unit 171 may further include a first upper projection 171*c* protruding from the central axis of the first disc 171*a* to an upper surface of the first disc 171*a*.

The second heat transfer unit 172 may be formed of oxygen-free copper, and may include a second disc 172*a*, a second upper projection 172*b* protruding from a central axis of the second disc 172*a* to an upper surface of the second disc 172*a*, and a second lower projection 172*c* protruding from the central axis of the second disc 172*a* to a lower surface of the second disc 172*a*. The second upper projection 172*b* of the second heat transfer unit 172 may have a screw groove 172*d* for coupling to the first lower projection 171*b* of the first heat transfer unit 171. The second lower projection 172*c* of the second heat transfer unit 172 may have a screw groove 172*e* for coupling to the third upper projection 173*b* of the third heat transfer unit 173.

The third heat transfer unit 173 may be formed of oxygen-free copper, and may include a third disc 173*a*, a third upper projection 173*b* protruding from a central axis of the third disc 173*a* to an upper surface of the third disc 173*a*, and a third lower projection 173*c* protruding from the central axis of the third disc 173*a* to a lower surface of the third disc 173*a*. The third lower projection 173*c* of the third heat transfer unit 173 may have a screw groove 173*d* for coupling to a fourth upper projection 174*b* of the fourth heat transfer unit 174.

The fourth heat transfer unit 174 may be formed of oxygen-free copper, and may include a fourth disc, the fourth upper projection 174*b* protruding from a central axis of the fourth disc to an upper surface of the fourth disc. A lower surface of the fourth heat transfer unit 174 may be coupled to a fixing means 178. The fixing means 178 may fix and cool the litz wire 12 connected to the SQUID sensor module 103*a*.

The first thermal expansion control unit 176 may be formed of an insulating material, and may be inserted between the first disc 171*a* of the first heat transfer unit 171 and the second disc 172*b* of the second heat transfer unit 172. The first thermal expansion control unit 176 may be formed of the same material as the internal container 160.

The second thermal expansion control unit 177 may be formed of an insulating material, and may be inserted between the third disc 173*a* of the third heat transfer unit 173 and the fourth disc 174*a* of the fourth heat transfer unit 174. The second thermal expansion control unit 177 may be formed of the same material as the internal container 160.

The first thermal expansion control unit 176 may include a first insulating body portion 176*a* having the same diameter as a first diameter D1 of the first disc 171*a*; a second insulating body portion 176*b* embedded in a lower surface of the internal body and having a second diameter D2 greater than the first diameter D1, and a third insulating body portion 176*c* having a third diameter D3 smaller than the second diameter D2. The third insulating body portion 176*c* may be disposed to cover an external circumferential surface of the second disc 172*a*. The external circumferential surface of the third insulating body portion 176*c* may have a screw groove.

The second thermal expansion control unit 177 may have the same structure as the first thermal expansion control unit 176.

The main thermal anchor 170 may cool the first SQUID sensor module 103*a* and the second SQUID sensor module 103*b* through a litz wire.

Each of the first SQUID sensor modules 103*a* may be cooled by a plurality of litz wires 12. Some of the plurality of litz wires 12 may be provided to a neighboring first SQUID sensor module 103*a*. The remainder of the plurality of litz wires 12 may be in thermal contact with the main thermal anchor 170.

Each of the first SQUID sensor modules 130*a* may be cooled by six litz wires. Two litz wires 12 may be in thermal contact with the main thermal anchor, and the other four litz wires 12 may be connected to a neighboring first SQUID sensor module 103*a*.

Each of the first SQUID sensor modules 103*a* may be inserted into a through-hole, formed in the first sensor-mounted helmet 122, to be fixed.

The first SQUID sensor module 103_a_ may include a plurality of holes 611. The litz wire 12 may be inserted into the holes 611 to cool the SQUID sensor 646.

Figure 17A:
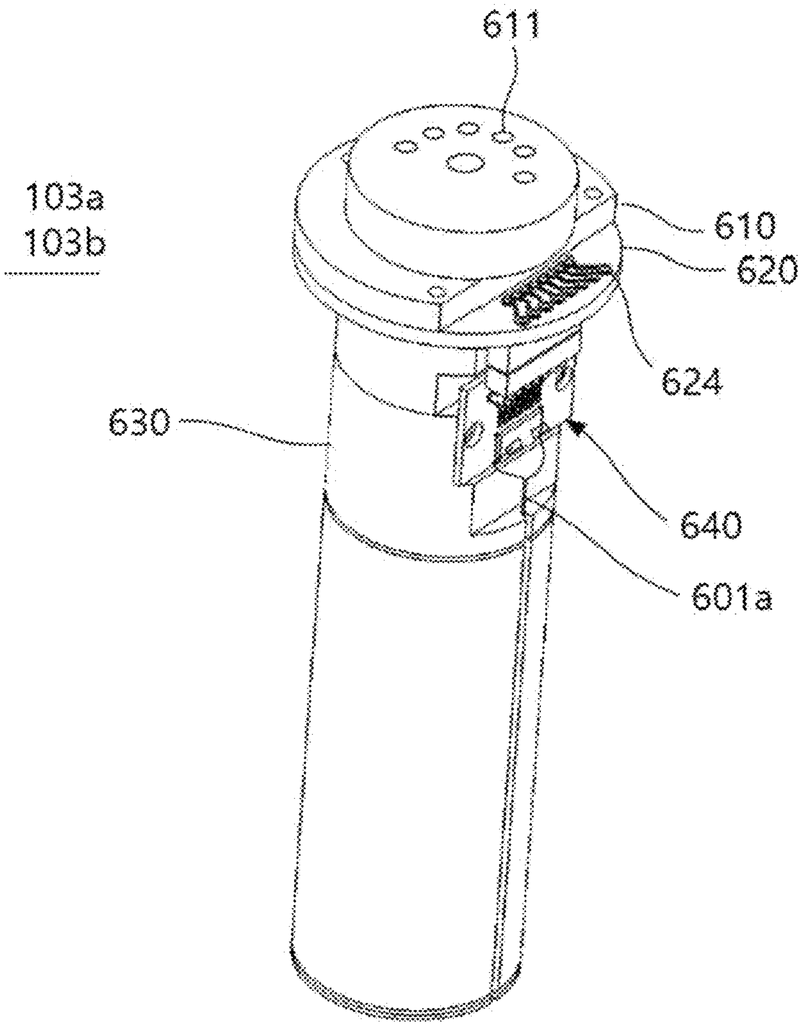
FIG. 17A is a perspective view illustrating a SQUID sensor module according to an example embodiment of the present disclosure.

FIG. 17A is a perspective view illustrating a SQUID sensor module according to an example embodiment of the present disclosure.

Figure 17B:
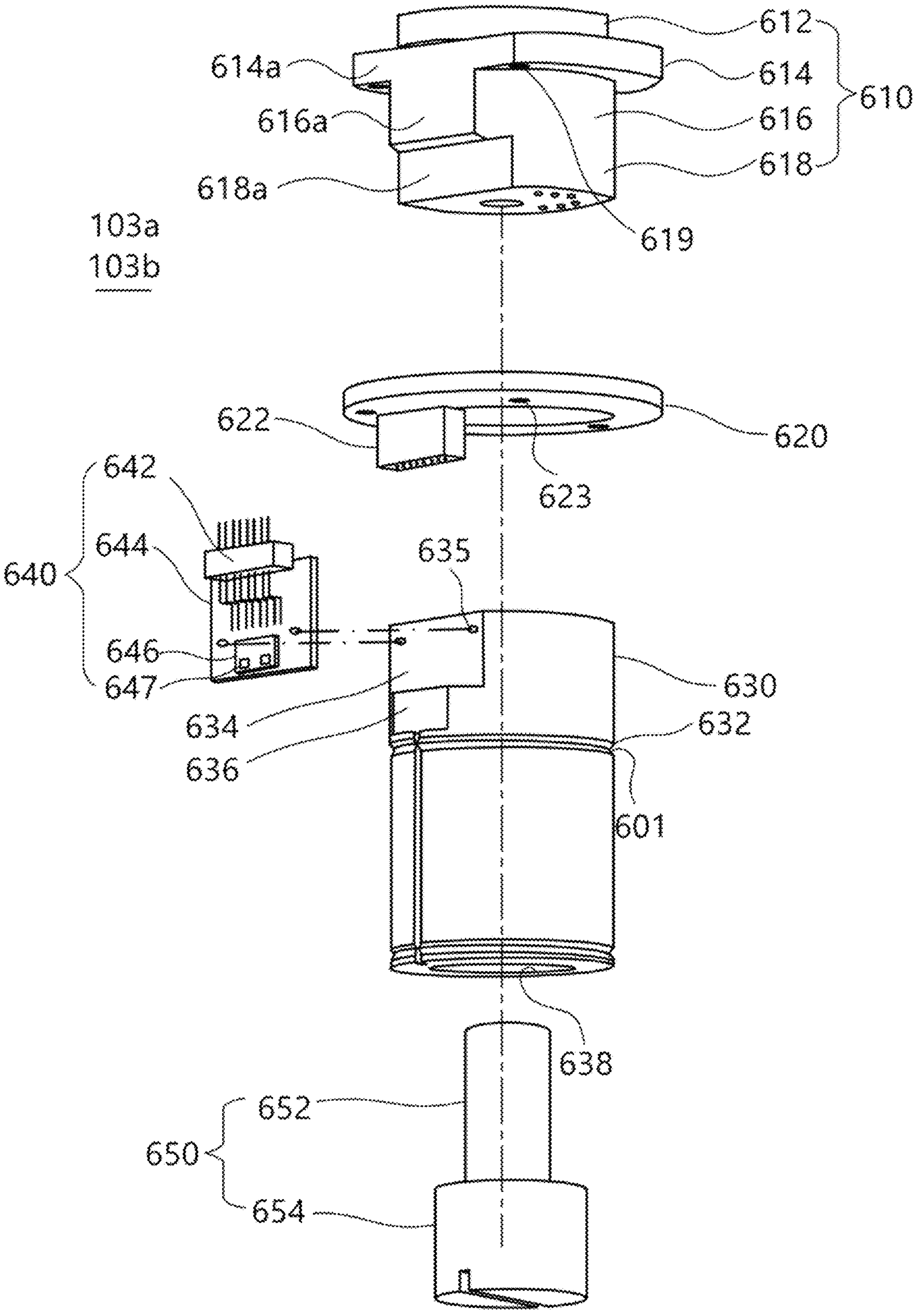
FIG. 17B is an exploded perspective view illustrating the SQUID sensor module in FIG. 17A.

FIG. 17B is an exploded perspective view illustrating the SQUID sensor module in FIG. 17A.

Figure 17C:
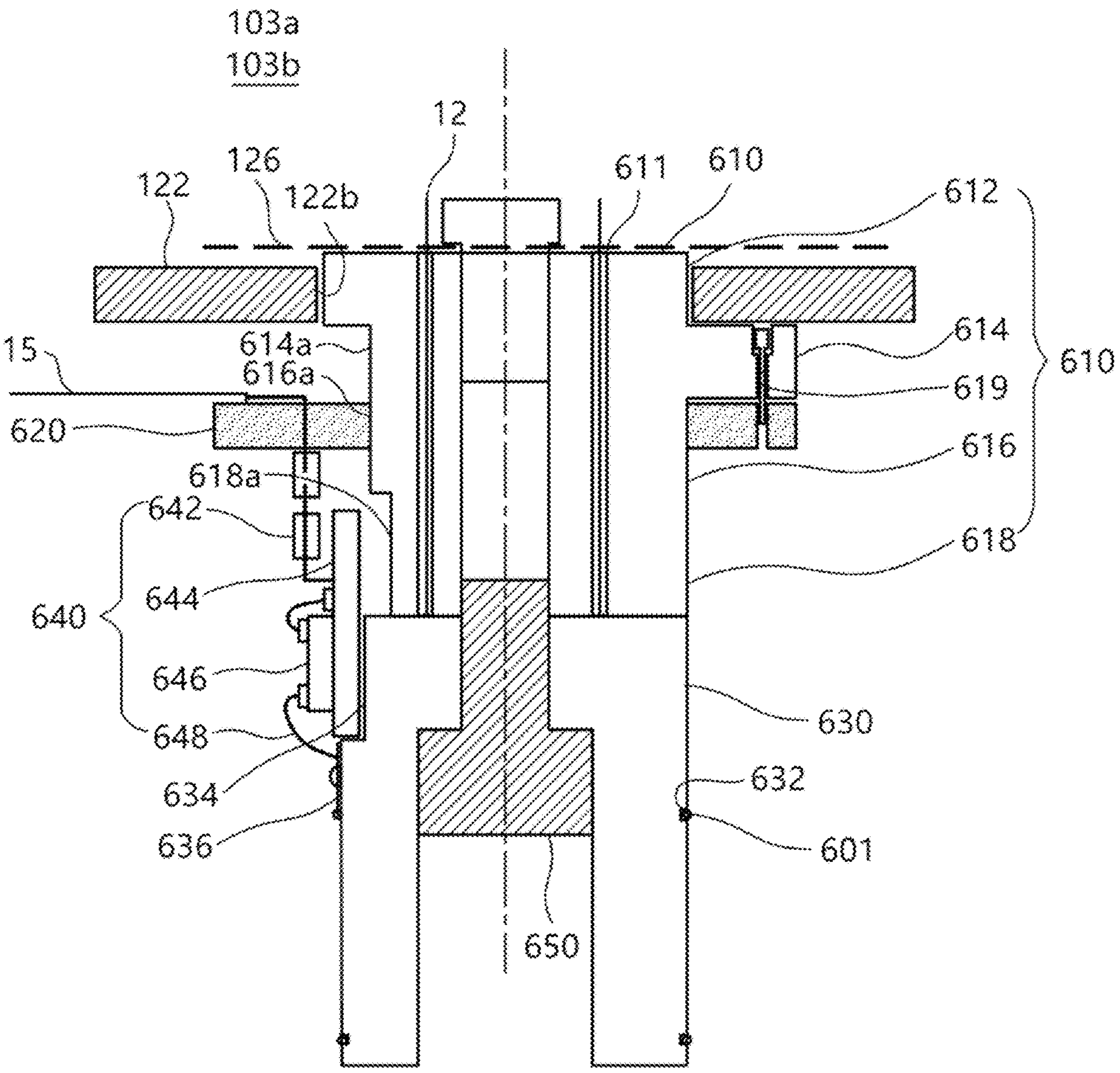
FIG. 17C is a cross-sectional view illustrating a SQUID sensor module according to an example embodiment of the present disclosure.

FIG. 17C is a cross-sectional view illustrating a SQUID sensor module according to an example embodiment of the present disclosure.

Referring to FIGS. 17A to 17C, a SQUID sensor module 103_a_/103_b_ may include a fixed block 610 having one end fixed to a sensor-mounted helmet 122/132, a bobbin 630 having one end coupled to the other end of the fixed block 610 and provided with a groove around which a pick-up coil 601 is wound, a bobbin fixing means 650 fixed to the other end of the fixed block 610 through a through-hole formed in a center of the bobbin 630, a superconducting quantum interference device (SQUID) printed circuit board (PCB) 640 disposed on an upper side surface of the bobbin 630 and including a SQUID sensor 646, and a signal line connection PCB 620 inserted into an external circumferential surface of the fixed block 610 and transferring a signal, detected by the SQUID sensor 646, to an external circuit.

The sensor-mounted helmets 122 and 132 may mount a SQUID sensor module 600, and may be disposed in a vacuum space between an external container and an internal container. The sensor-mounted helmets 122 and 132 may be formed of a non-magnetic material. The sensor-mounted helmets 122 and 132 may include a first sensor-mounted helmet 322 and a second sensor-mounted helmet 332 mounting a SQUID sensor module.

The fixed block 610 may be formed of a non-magnetic material, such as G10 epoxy, in an integral type. The fixed block 610 may be inserted into the through-hole 122_b_ formed in the sensor-mounted helmet to be fixed through an adhesive. The fixed block 610 may include a fixed block projection 612, a fixed block threshold portion 614, a fixed block body portion 616, and a fixed block extending portion 618. The fixed block 610 may have a plurality of holes 611 in a central axis direction in which a litz wire for cooling is inserted. The litz wire may be inserted into each of a plurality of holes 611 to cool the SQUID sensor 646.

The fixed block projection 612 may have a disc shape, and may be coupled to a groove or a through-hole 122_b_ formed in the sensor-mounted helmet. In addition, the fixed block projection 612 may be fixed to the through-hole through an adhesive.

The fixed block threshold portion 614 may have a disc shape and may be continuously connected to the fixed block projection portion 612. The fixed block threshold portion 614 may have a greater diameter than the fixed block projection 612. The fixed block threshold portion 614 may have a planar side surface 614_a_. One side surface 614_a_ of the fixed block threshold 614 may be a plane having a predetermined first vertical distance from a central axis having a cylindrical shape. The fixed block threshold portion 614 may serve to perform an alignment in a central axis direction. A through-hole 619 may be formed in an exterior of the fixed block threshold 614.

The fixed block body portion 616 may be a portion coupled to the signal line connection PCB 620. The signal line connection PCB 620 may be disposed to be inserted into the external peripheral surface of the fixed block body portion 616. The signal line connection PCB 620 may include a hole 623 on an external periphery thereof. The through-hole 619 of the fixed block threshold 614 may be aligned with the hole 623 of the signal line connection PCB 620. The fixing means may be inserted into the through-hole 619 of the fixed block threshold portion 614 and the hole 623 of the signal line connection PCB 620 to fix the fixed block threshold portion 614 and the signal line connection PCB 620 to each other. An internal diameter of the signal line connection PCB 620 may be substantially the same as an external diameter of the fixed block body portion 616. In addition, the external diameter of the signal line connection PCB 620 may be substantially the same as an external diameter of the fixed block threshold 614.

The signal line connection PCB 620 has a washer shape having a central through-hole therein. When the signal line connection PCB 620 is coupled to the external circumferential surface of the fixed block 610, one side of the central through-hole may be planar so as to inhibit a rotational motion. The signal line connection PCB 620 may include a first connector 622. The first connector 622 may be a female connector. The first connector 622 may be disposed on an edge of a lower surface of the signal line connection PCB 620. A connection terminal 624 and a wiring may be disposed on an upper surface of the signal line connection PCB 620. The connection terminal 624 may be connected to the first connector 622 through the wiring. A connection wire, connected to an external circuit, may be coupled to the connection terminal 624.

The fixed block body portion 616 may have a disc shape and may be continuously connected to the fixed block threshold portion 614. The fixed block body portion 616 may have a smaller diameter than the fixed block threshold portion 614, and may have a planar side surface 616_a_. One side surface 616_a_ of the fixed block body portion 616 may be a plane having a predetermined second vertical distance from the central axis having a cylindrical shape.

The fixed block extending portion 618 may have the same diameter as the fixed block body portion 616, and may have a planar side surface 618_a_. The side surface 618_a_ may be a plane having a predetermined third vertical distance from the central axis having a cylindrical shape. The third vertical distance may be smaller than the second vertical distance.

One planar side surface 614_a_ of the fixed block threshold portion 614 and one planar side surface 616_a_ of the fixed block body portion 616 may be connected to each other. The one side surface 616_a_ of the fixed block body 616 and the one side surface 618_a_ of the fixed block extending portion 618 may be spaced apart from each other to be parallel to each other. A vertical distance between a central axis and one side surface of the fixed block extending portion 618 may be smaller than a vertical distance between the central axis and one side surface of the fixed block body portion 616.

The bobbin 630 may be formed of a non-magnetic material such as G10 epoxy. The bobbin 630 may have a cylindrical shape. The bobbin 630 includes a first planar portion 634, formed on an upper side surface having a first vertical distance from the central axis, and a second planar portion 634 formed on a lower side surface 636 having a second vertical distance larger than the first vertical distance. The bobbin 630 may have a groove 632 formed around a lower side surface thereof. The groove may form a closed loop. A pick-up coil 601 may be wound around the groove 632. A hole 635 may be formed in the first planar portion 634. The hole 635 may be coupled to a fixing means for fixing the SQUID PCB 640. The SQUID PCB 640 may be disposed on the first planar portion 634. Both ends of the pick-up coil 601 may be fixed to the second planar portion 636 through an adhesive. The pick-up coil 601 may be electrically connected to the SQUID sensor 646 through a connection line 648 formed of a superconductor material. The connection line 648 may include a niobium (Nb) material.

The SQUID PCB 640 may include a second connector 642 and a SQUID sensor 646 and disposed on a PCB substrate 644. The SQUID sensor 646 may be in the form of a semiconductor chip. The SQUID sensor 646 may include an input coil and a Josephson junction. The SQUID sensor 646 may include a conductive pad for electrical connection to the pick-up coil 601. The conductive pad may connect the pick-up coil 601. The second connector 642 may be electrically connected to another conductive pad. The second connector 642 may be a pin-type male connector. Accordingly, the second connector 642 may be separated from or coupled to the first connector 622.

The pick-up coil 601 may be a first-order axial gradiometer. Therefore, a length of a bobbin, around which the pick-up coil 601*a* is wound, may be increased. The pick-up coil 601 may include a pair of one-turn coils continuously connected and wound in directions opposite to each other. The pick-up coil 601 and the SQUID sensor 646 are bonded to be directly connected to each other using a connection line 648 of a thermally treated superconducting material, and an integral-type QUID magnetometer may be manufactured. A material of the pick-up coil 601 may be a niobium-tantalum (NbTi) wire.

The connection line of a niobium (Nb) material, used for bonding, may be subject to a vacuum heat treatment at a temperature 1900 degrees Celsius to increase ductility. Superconducting bonding may be performed using an ultrasonic wedge bonder. Both end portions of the pick-up coil may be twisted together. Accordingly, noise of the pick-up coil may be significantly reduced. The pick-up coil may be a first-order gradiometer or a magnetometer.

The bobbin fixing means 650 may be inserted into a through-hole 638 penetrating through a central axis of the bobbin 630. Thus, the bobbin fixing means 650 may be fixed to a lower surface of the fixed block 610. The bobbin fixing means 650 may include a non-magnetic material such as G10 epoxy.

When the SQUID PCB 640 malfunctions, the bobbin fixing means 650 may be removed to replace the SQUID PCB 640. In this case, the bobbin 630 and the fixed block 610 may be separated from each other. Thus, the malfunctioning SQUID PCB may be simply replaced with a new SQUID PCB. As a result, maintenance may be facilitated.

The SQUID sensor module 103*a*/103*b* may include a fixed block 610 having one end fixed to a support portion, a bobbin 630 having one end coupled to the other end of the fixed block 610 and having a groove around which a pick-up coil 601*a* is wound, a bobbin fixing means fixed to the other end of the fixed block 610 through a through-hole formed in a center of the bobbin 630, a superconducting quantum interference device (SQUID) printed circuit board (PCB) 640 including a SQUID sensor, and a signal line connection PCB 620 inserted into an external circumferential surface of the fixed block 610 and transferring a signal, detected by the SQUID sensor, to an external circuit.

Figure 18:
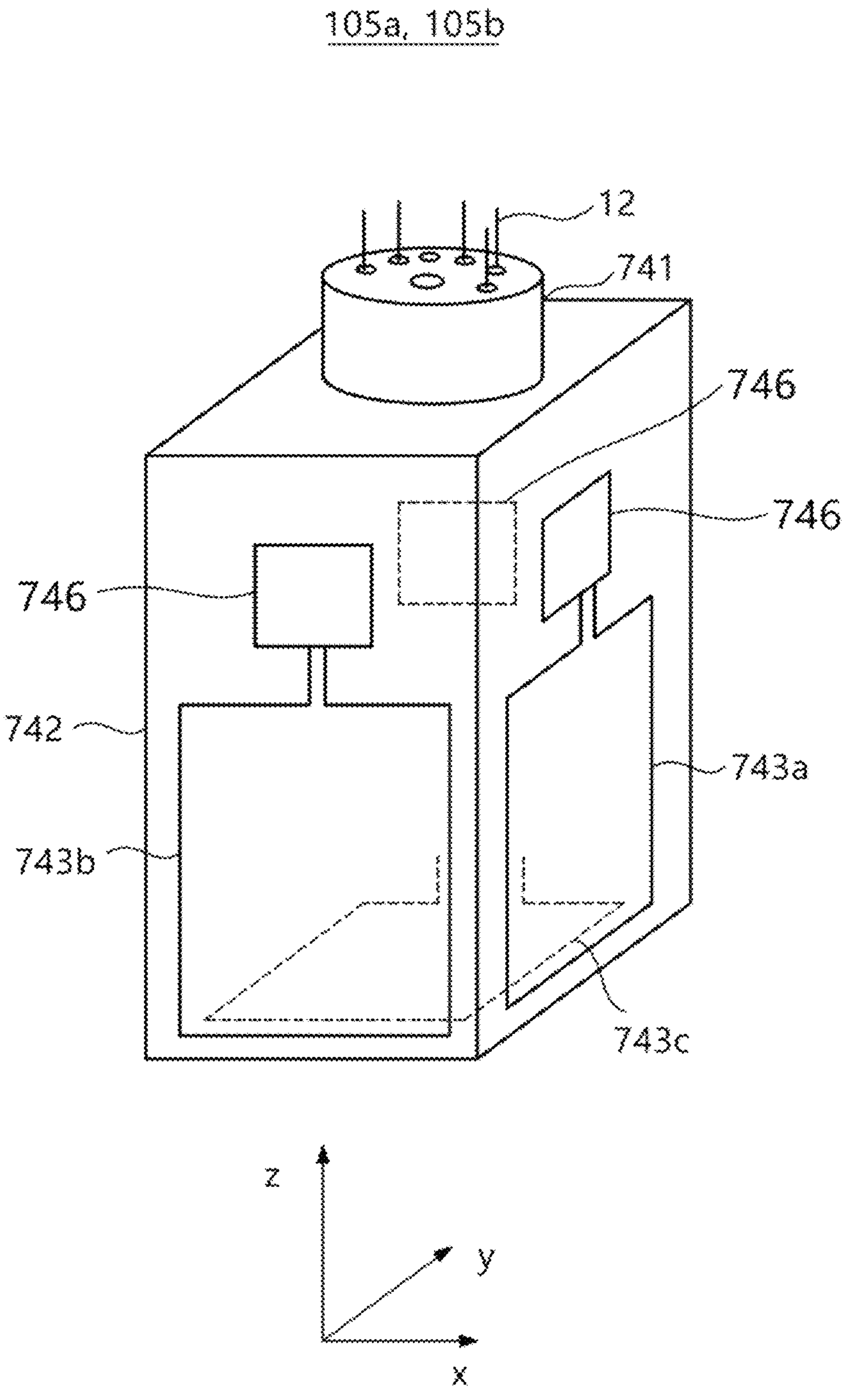
FIG. 18 is a perspective view illustrating a reference SQUID sensor module according to another example embodiment of the present disclosure.

FIG. 18 is a perspective view illustrating a reference SQUID sensor module according to another example embodiment of the present disclosure.

Referring to FIGS. 6A and 18, the first reference SQUID sensor module 105*a* may be disposed on the first sensor-mounted helmet 122, and the second reference SQUID sensor module 105*b* may be disposed on the second sensor-mounted helmet 132. The first reference SQUID sensor module 105*a* may be used as a sensor measuring a background magnetic field while the second SQUID sensor module 103*b* operates. The second reference SQUID sensor module 105*b* may be used as a sensor measuring a background magnetic field while the first SQUID sensor module 103*a* operates.

The first reference SQUID sensor module 105*a* and the second reference SQUID sensor module 105*b* may be a triaxial magnetic field sensor. Each of the first reference SQUID sensor module 105*a* and the second reference SQUID sensor module 105*b* may include a first pick-up coil 743*a* detecting a magnetic field component in an x-axis direction, and a second pick-up coil 743*b* detecting a magnetic field component in a y-axis direction, and a third pick-up coil 743*c* detecting a magnetic field component in a z-axis direction. Each of the first to third pick-up coils 743*a* to 743*c* may be connected to the SQUID sensor 746.

The first reference SQUID sensor module 105*a* may include a cylindrical fixing block 741 and a bobbin 742 in which a pick-up coil, coupled to the fixing block 741, is disposed. The bobbin 742 may have a cuboidal shape. The fixing block 741 may include a plurality of through-holes in a central axis direction, and the litz wire 12 may be inserted into the through-holes. The litz wire 12 may be connected to a main thermal anchor 170.

As described above, a magnetoencephalography measuring apparatus according to an example embodiment may measure magnetoencephalography of adults or children using a helmet for children and a helmet for adults, respectively disposed on both ends of a Y-shaped Dewar slantly disposed in a narrow magnetically shielded room.

A magnetoencephalography measuring apparatus according to an example embodiment may efficiently block radiant heat using a neck portion having a double-wall structure in a Y-shaped Dewar slantly disposed.

A magnetoencephalography measuring apparatus according to an example embodiment may measure magnetoencephalography of adults or children by placing a rotational motion unit, providing a rotational motion in a Y-shaped Dewar slantly disposed, on the ground.

A magnetoencephalography measuring apparatus according to an example embodiment may increase efficiency of a condenser or a cooler by transferring a low-temperature refrigerant to the condenser while providing a rotational motion using a coaxial dual-tube structure connecting the condenser and a Dewar to each other.

A magnetoencephalography measuring apparatus according to an example embodiment may employ a coil-in-vacuum (CIV) structure such that a distance between a SQUID sensor and a current source may be reduced to increase a signal-to-noise ratio (SNR).

A magnetoencephalography measuring apparatus according to an example embodiment may include a main thermal anchor for cooling a SQUID sensor on a lower surface of an internal container storing a refrigerant. The main thermal anchor may include of a plurality of components to increases a thermal contact area while inhibiting damage to the internal container caused by thermal expansion, and thus, may efficiently cool a litz wire and a SQUID sensor.

Although the present disclosure and its advantages have been described in detail, it should be understood that various changes, substitutions and alterations can be made herein without departing from the spirit and scope of the disclosure as defined by the following claims.

What is claimed is:

1. A magnetic field measuring apparatus comprising:

an external container; and an internal container storing a liquid refrigerant and in the external container;

wherein the internal container comprises:

a neck portion;

a baffle insert in the neck portion; and a body portion having an increased diameter as compared with the neck portion, wherein the neck portion has a double-wall structure including an internal cylinder, an external cylinder surrounding the internal cylinder, and a heat shielding layer between the internal cylinder and the external cylinder configured to reduce influx of radiant heat from the neck portion, and when the interior container is cooled, the double-wall structure automatically forms a vacuum layer.

2. The magnetic field measuring apparatus as set forth in claim 1, wherein the internal cylinder further comprises a plurality of ring projections protruding outwardly from an external surface of the internal cylinder, thermal anchors are coupled to the ring projections, respectively, the ring projections are spaced apart from each other, and the external cylinder is divided with the ring projections interposed therebetween.

3. The magnetic field measuring apparatus as set forth in claim 2, wherein each of the thermal anchors has a plurality of radial slits therein, extending internally from an external circumferential surface.

4. The magnetic field measuring apparatus as set forth in claim 2, wherein an external circumferential surface of the ring projections and an internal circumferential surface of the thermal anchors are screw-coupled to each other.

5. The magnetic field measuring apparatus as set forth in claim 2, wherein the thermal anchor includes a thermal anchor coupling portion and a disc-shaped thermal anchor body portion on an external circumferential surface of the thermal anchor coupling portion, and an internal circumferential surface of the thermal anchor coupling portion is screw-coupled to an external circumferential surface of the ring projections.

6. The magnetic field measuring apparatus as set forth in claim 5, wherein each of the thermal anchors has an azimuthal groove at an internal end of each of the slits.

7. The magnetic field measuring apparatus as set forth in claim 2, wherein the thermal anchors comprise first to third thermal anchors, and wherein the first thermal anchor is connected to a 120K heat shielding layer, the second thermal anchor is connected to an 80K heat shielding layer, and the third thermal anchor is connected to a 40K heat shielding layer.

8. The magnetic field measuring apparatus as set forth in claim 1, further comprising:

a refrigerant exhaust tube at the baffle insert, configured to exhaust an evaporated refrigerant;

a refrigerant injection tube at the baffle insert, configured to inject a refrigerant; and a condenser connected to the refrigerant exhaust tube and the refrigerant injection tube, configured to condense the evaporated refrigerant exhausted through the refrigerant injection tube.

9. The magnetic field measuring apparatus as set forth in claim 8, wherein each of the refrigerant exhaust tube and the refrigerant injection tube comprises a dual tube, and the dual tube includes an internal tube and an external tube.

10. The magnetic field measuring apparatus as set forth in claim 9, wherein the refrigerant exhaust tube and the refrigerant injection tube are coaxial.

11. The magnetic field measuring apparatus as set forth in claim 1, further comprising:

a main thermal anchor on a lower surface of the internal container; and a plurality of first SQUID sensor modules outside the internal container, wherein each of the plurality of first SQUID sensor modules is in thermal contact with the main thermal anchor.

12. The magnetic field measuring apparatus as set forth in claim 11, wherein the plurality of SQUID sensor modules is cooled by a plurality of litz wires, and a subset of the plurality of litz wires is in thermal contact with the main thermal anchor.

13. The magnetic field measuring apparatus as set forth in claim 11, wherein each of the plurality of SQUID sensor modules is in thermal contact with the main thermal anchor through a corresponding litz wire.

14. The magnetic field measuring apparatus as set forth in claim 11, wherein the main thermal anchor comprises a conductive heat transfer material.

15. The magnetic field measuring apparatus as set forth in claim 1, further comprising a first washer-shaped thermal anchor, a second washer-shaped thermal anchor, and a third washer-shaped thermal anchor, wherein each of the first, second and third washer-shaped thermal anchors is outside the neck portion and vertically spaced apart from each other.

16. The magnetic field measuring apparatus as set forth in claim 15, further comprising a 120K heat shielding layer connected to the first washer-shaped thermal anchor, an 80K heat shielding layer connected to the second washer-shaped thermal anchor, and a 40K heat shielding layer connected to the third washer-shaped thermal anchor.

17. The magnetic field measuring apparatus as set forth in claim 1, wherein the body portion stores the liquid refrigerant, and the liquid refrigerant is liquid helium.

18. The magnetic field measuring apparatus as set forth in claim 1, wherein the external container includes an external container lid with a through-hole in a center thereof, and the internal container is coupled to the through-hole of the external container lid.

* * * * *